United States Patent [19]
Okamoto et al.

[11] Patent Number: 5,679,516
[45] Date of Patent: Oct. 21, 1997

[54] PROCESS FOR DETECTING NUCLEIC ACID BY CAPILLARY ELECTROPHORESIS

[75] Inventors: Tadashi Okamoto, Yokohama; Takeshi Miyazaki, Ebina, both of Japan

[73] Assignee: Canon Kabushiki Kaisha, Tokyo, Japan

[21] Appl. No.: 317,872

[22] Filed: Oct. 4, 1994

[30] Foreign Application Priority Data

Oct. 4, 1993 [JP] Japan .................. 5-248211

[51] Int. Cl.$^6$ .............. C07H 21/04; C12Q 1/68; G01N 27/26
[52] U.S. Cl. .............. 435/6; 436/161; 436/800; 536/26.6; 204/452
[58] Field of Search ................ 435/6; 436/161, 436/800; 536/26.6; 204/180.1, 182.8

[56] References Cited

U.S. PATENT DOCUMENTS 5,268,486 12/1993 Waggoner et al. .............. 548/427
5,470,705 11/1995 Grossman et al. .............. 435/6

FOREIGN PATENT DOCUMENTS 2-191674 7/1990 Japan .
5-208200 8/1993 Japan .
6-230007 8/1994 Japan .

OTHER PUBLICATIONS

J. Sambrook et al., "Analysis and Cloning of Eukaryotic Genomic DNA", Molecular Cloning: A Laboratory Manual, 2nd ED, published by Cold Spring Harbor Laboratory Press, 1989, pp. 9.31–9.58.

Chen et al., Journal of Chromatography 559:295–305 1991.

Vilenchik et al., Journal of Chromatography (A) 663:105–113 Mar. 4, 1994.

Bianchi et al., Journal of Virological Methods 47(3):321–329 May 1994.

Chen et al. J. Chromatography A652 (1993) 355–360.

Matthews et al. Anal. Biochem. 169:1–25, 1988.

*Primary Examiner*—W. Gary Jones
*Assistant Examiner*—Paul B. Tran
*Attorney, Agent, or Firm*—Fitzpatrick, Cella, Harper & Scinto

[57] ABSTRACT

A process for detecting a target nucleic acid, which includes the steps of hybridizing a target single-stranded nucleic acid in a sample solution to a labeled single-stranded nucleic acid probe to form a reaction mixture containing a hybrid, subjecting the reaction mixture to capillary electrophoresis to separate the hybrid from the free labeled nucleic acid probe, and detecting the hybrid utilizing the label moiety of the nucleic acid probe constituting the hybrid.

10 Claims, 5 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (SYNTHESIZED POLYNUCLEOTIDE)

( x i ) SEQUENCE DESCRIPTION: SEQ ID NO:1:

GTTGTAAAAC GACGGCCAGT        20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (SYNTHESIZED POLYNUCLEOTIDE)

( x i ) SEQUENCE DESCRIPTION: SEQ ID NO:2:

```
ACTGGCCGTC GTTTTACAAC                                                    20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (SYNTHESIZED POLYNUCLEOTIDE)

( x i ) SEQUENCE DESCRIPTION: SEQ ID NO:3:

ACTGGCCGTC CTTTTACAAC                                                    20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (SYNTHESIZED POLYNUCLEOTIDE)

( x i ) SEQUENCE DESCRIPTION: SEQ ID NO:4:

ACTGGCGGTC GTTATACAAC                                                    20
```

PROCESS FOR DETECTING NUCLEIC ACID BY CAPILLARY ELECTROPHORESIS

BACKGROUND OF THE INVENTION

1. Field of the Invention

The present invention relates to a process for detecting and identifying a desired base sequence in the nucleic acid (DNA or RNA) of viruses, microorganisms, animals, plants, humans and the like, or detecting the presence of mutation in a certain base sequence.

2. Related Background Art

According to the development of techniques of nucleic acid analysis, various mutation genes have been discovered and the elucidation of various genetic diseases due to the gene mutation are in progress. Among these genetic diseases, it is now clarified that symptoms of certain diseases are caused by mutated proteins which result from the partial deletion or point mutation of the base sequence of a gene. At present, these genetic diseases are mainly detected, after the appearance of the symptoms, by an enzyme assay or an immunological method using an antibody. For the sake of early treatment, it is important to detect the presence of the gene mutation in the early stage before the appearance of serious symptoms.

One of the effective methods for the early detection is RFLP (restriction fragment length polymorphism). According to this method, for example, the total gene of a human is digested by restriction enzymes to obtain many DNA fragments, and these fragments are then separated by agarose gel electrophoresis, fixed on a filter according to Southern blotting, and then hybridized with a DNA or RNA probe labeled with a radioisotope or the like. Thus, from the difference of the digestion patterns of normal DNA and the specimen DNA, the presence of the gene related to the disease can be detected.

Furthermore, the DNA diagnosis is not only used for the human genome but also for the identification of pathogenic bacterium in an infection disease.

A conventional identification of a bacterium not using gene analysis is carried out by comparing its morphology and biochemical characteristics of the bacterium isolated from the patient with those of known bacteria, based on the similarity. This method, however, has problems that cultivation is much time-consuming, the characteristics may be differently determined when different test methods are used, and that the result of identification may vary according to the characteristic thought important.

In recent years, particularly in the field of detection and identification of pathogenic bacteria in bacterial infections, DNA-DNA or DNA-RNA hybridization techniques have been tried. In this method, the nucleic acid (DNA or RNA) is extracted from a bacterium, and then by utilizing the hybridization method, the presence of a specific base sequence in the sample nucleic acid (which has high homology to a specific part of the nucleic acid of the standard bacterium) is used to determine the presence of a certain bacterium in the sample.

The basic technique, the hybridization method, usually consists of the following steps, as described in "Molecular Cloning" (1989), Maniatis et al.

(1) A step of digestion of the nucleic acid containing the target portion with suitable restriction enzymes, followed by separation of the thus obtained fragments by slab gel electrophoresis.

(2) A step of transferring the separated nucleic acid fragments to be adsorbed onto a nitrocellulose filter (the Southern blot technique).

(3) A step of reacting the nitrocellulose filter obtained in the step (2) with a nucleic acid probe to form a hybrid of the probe and the target nucleic acid.

(4) A step of washing and removing the probes which did not form a hybrid.

(5) A step of detecting DNA fragments hybridized with the probe.

The above-mentioned ordinary hybridization method has the following problems.

(1) Basically, the separation is carried out with a slab gel and the detection on the filter. Therefore, transfer and adsorption process of the nucleic acid from the gel to the filter is required. These operations are very intricate and time-consuming.

(2) It is necessary to remove the nucleic acid probe not specifically adsorbed to the filter. For this removal operation, strictly controlled conditions are required, as well as skill and time.

In addition, the washing operation may strongly affect the detection sensitivity, so that it must be carried out with care.

(3) The separation is done by slab gel electrophoresis, and the transfer efficiency of the nucleic acid from the gel to the filter is as low as several tens percent. Hence, a relatively large sample amount is required on the whole.

(4) As a detection means, the nucleic acid probe labeled with a radioisotope is used for detection by autoradiography. Although this method is highly sensitive, it has a drawback that radioisotopes are harmful to human health. Other detection means includes a method to detect a luminous substance by autoradiography, such as DIG-AMPPD method (Boehringer Mannheim Yamanouchi Co., Ltd.), and more popular NBT-BCIP method. However, these methods require a step for development of luminescence or color, and therefore they have a problem that time is taken for the detection.

SUMMARY OF THE INVENTION

The present invention solves the problems of conventional nucleic acid detection methods utilizing a hybridization technique providing process for detecting the nucleic acid without intricate operations requiring skill and a long period of time as in conventional methods. Another object of the present invention is to provide a method of high sensitivity to detect nucleic acid even with a small amount of samples.

The method for detecting nucleic acid of the present invention by which the above-mentioned objects can be accomplished comprises steps of:

(1) reacting target nucleic acid with a labeled nucleic acid probe prepared for the detection of the target nucleic acid in a solution under conditions suitable for hybridization thereof, to obtain a reaction mixture, (2) subjecting thus obtained reaction mixture to capillary electrophoresis to separate the hybrid from the unreacted labeled probe, and (3) detecting the hybrid utilizing the label of the probe constituting the hybrid.

DETAILED DESCRIPTION OF THE PREFFERRED EMBODIMENTS

Figure 1:
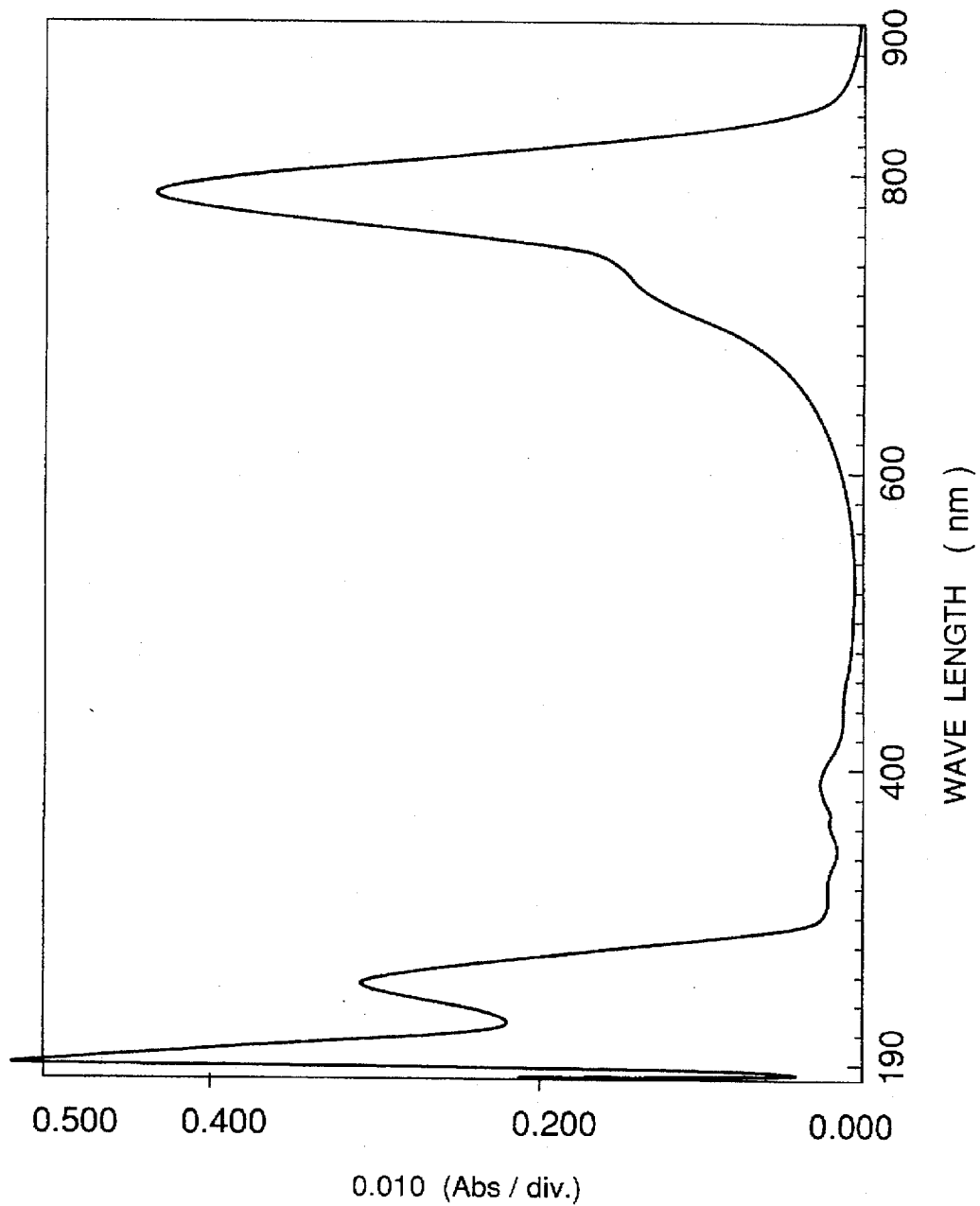
FIG. 1 shows an absorption spectrum of Compound No. 5.

In the present invention, the target nucleic acid and a labeled nucleic acid probe specific for the target nucleic acid are put in a solution under hybrid forming conditions, and then separated by capillary electrophoresis. As a result of this capillary electrophoresis, hybrids of the target nucleic acid and the nucleic acid probe are separated from the free nucleic acid probe which did not hybridize, and are then detected.

The nucleic acid probe which can be used in the present invention has a base sequence which is complementary to all or a part of a base sequence of the target nucleic acid, and the utilizable nucleic acid probe includes natural DNA, RNA and fragments thereof, partially changed base sequences or modified base sequences thereof, and synthetic DNA and RNA.

In the present invention, the target nucleic acid is first reacted with the labeled nucleic acid probe. This reaction is carried out in a solution under conditions suitable for the hybrid formation. As factors affecting hybrid formation, there are salt concentration, pH, base composition and length of the target nucleic acid and the nucleic acid probe, and reaction temperature. They can be selected in compliance with the kind of target nucleic acid and nucleic acid probe, reagents, the buffer solution and the like. In particular, the reaction temperature is preferably controlled so as to be in a range where the formation and stability of the aimed hybrid can be secured.

As a solution in which the reaction between the target nucleic acid and nucleic acid probe is carried out, there are various usual buffer solutions suitable for the hybridization method.

After the completion of reaction between the target nucleic acid and the nucleic acid probe, the thus obtained reaction mixture is subjected to capillary electrophoresis. In general, in capillary electrophoresis, molecules move in order of molecular weight. As a consequence, in the case of the present invention, the nucleic acid probe and the target nucleic acid move faster, and afterward, the hybrid of the nucleic acid probe and the target nucleic acid move, so that they are separated from each other.

Either type of capillary loaded with or without gel can be used in compliance with the length of the target nucleic acid, the length of the nucleic acid probe, the kind of the label for the probe, and the like. In the present invention, the reaction mixture of the target nucleic acid and the nucleic acid probe is directly separated by capillary electrophoresis followed by detection. Therefore, complex operations which require skill and time as in conventional techniques can be saved.

A sufficient amount of a sample for capillary electrophoresis iS several nl. The transfer of the sample from the gel to the filter as in the conventional techniques is not necessary, and so loss of the sample is minimized. Hence, the detection can be achieved with an extremely small amount of the sample.

The hybrid of the nucleic acid probe and the target nucleic acid which has been separated by capillary electrophoresis is detected utilizing the label attached to the nucleic acid probe. Detection can be carried out at a specific site of the capillary, or at a flow cell device to which the eluate is led.

The formation and stability of the hybrid are affected by the temperature conditions to which the hybrid has been exposed. That is to say, the hybrid formation temperature and a hybrid melting temperature (a temperature at which the hybrid dissociates into two single strands) often depend upon the base composition of the nucleic acid constituting the hybrid. Thus, by selecting the temperature condition for the reaction the target nucleic acid with the nucleic acid probe, the formation of mismatched hybrids can be prevented. That is, nucleic acids other than the target nucleic acid and the nucleic acid probe cannot form non-specific double-strands. Furthermore, even if the mismatched hybrids are formed, the reduction of detection accuracy due to the contamination with the mismatched hybrids can be prevented by employing the temperature conditions at which the mismatch hybrids melt but the desired hybrid does not melt.

This can be said for processes of capillary electrophoresis and detection of the aimed hybrid. Therefore, the influence of the mismatched hybrids on the detection accuracy can be eliminated by controlling the temperature conditions at least in one of the above-mentioned steps (1) to (3).

In general, at least one mismatched base pair is present in a mismatched hybrid, which reduces its stability so that the hybrid separates into single strands at lower temperature in comparison with the hybrid of complete complementarity. Therefore, the formation of the mismatched hybrids can be prevented by using a temperature higher than the melting temperature of the mismatched hybrids and lower than the melting temperature of the desired hybrid. Thus, if the respective steps are performed at a temperature, for example, about 5° to 25° C. lower than the melting temperature of the desired hybrid, the formation of the mismatch hybrid can be prevented, although it depends upon the kinds of target nucleic acid and nucleic acid probe, operating conditions and the like.

Even when the mismatched hybrids are formed, the contamination of the mismatched hybrids can be prevented by utilizing the difference between the melting temperature of the mismatched hybrids and that of the target hybrid. For example, when the temperature is slowly raised from a temperature necessary to melt the mismatched hybrids having the lowest melting temperature to a temperature at which the mismatched hybrid having the highest melting temperature melts but the target hybrid does not, the single strands are formed from the mismatched hybrids in order of instability, and migrate faster than the target hybrid, whereby contamination of the target hybrid is prevented. This temperature control may be carried out in the step (1) or (3).

As a labeling technique and a detection technique of the nucleic acid probe which can be used in the present invention, conventional methods can be selected and utilized in compliance with the intended detecting operation. It is preferable to select a label having a desirable detection sensitivity and a detection method in consideration of use of capillary electrophoresis. In particular, the fluorescence method is preferable in view of simplicity, stability, sensitivity and the like.

When the fluorescence method is used, a fluorescent label compound having absorption and fluorescence at wavelength of 600 nm or more is preferably used in order to prevent sensitivity reduction due to the contamination of the fluorescent biomaterials. Moreover, in order to prevent heat generation due to emission light, it is preferable to employ the label compound and the detection method to which an excitation light source of 1000 nm or less can be applied.

From these viewpoints, the present inventors investigated characteristics of fluorescent dyes having an absorption maximum and a fluorescence maximum in the wavelength range of 600 to 1000 nm. There are quite few commercial dyes having the absorption maximum and the fluorescence maximum in the wavelength range of 600 to 1000 nm. One of the few available examples is Rhodamine NIR-1, a product of Dojin Chemical Laboratory Co., Ltd. (the absorption maximum=662 nm, and the fluorescence maximum= 692 nm), but this dye lacks proper storage stability and stability under capillary electrophoresis conditions. As another example of the available fluorescent dye, there is a cyanine dye Cy5 made by Funakoshi Chemical Co., Ltd. (the absorption maximum=652 nm, and the fluorescence maximum=667 nm). The present inventors synthesized cyanine dyes including Cy5, which are applicable at long wavelengths, and their characteristics were then evaluated. Also the characteristics under capillary electrophoresis conditions of azulene dyes and tri-nuclear type dyes were estimated, which dyes had been already been determined by the present inventors to be desirable to label the nucleic acid probe in Japanese Patent Application Nos. 4-15665 and 5-19057.

As a result, it was concluded that cyanine dyes represented by the general formula I, trinuclear type dyes represented by the general formulae II and III, and azulene dyes represented by the general formula IV were desirable as a fluorescent label compound for the nucleic acid probe to be used in capillary electrophoresis.

Next, these dyes will be described in more detail.

The cyanine dyes to be used in the present invention are represented by the following general formula (I)

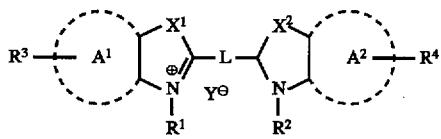

wherein $X^1$ and $X^2$ are each independently oxygen, sulfur, selenium, C=O, CH=CH, $NR^5$ or $CR^6R^7$ wherein $R^5$ to $R^7$ are each independently an alkyl group, an aryl group or an aralkyl group; $A^1$ and $A^2$ are each independently an aromatic ring comprising carbon and hydrogen, or an aromatic ring comprising carbon, hydrogen, nitrogen and/or oxygen and/or sulfur; $R^1$, $R^2$, $R^3$ and $R^4$ are each independently hydrogen, a halogen, a substituted or unsubstituted alkyl group, an alkoxy group, a substituted or unsubstituted aryl group, or a substituted or unsubstituted amino group; L is a methine chain comprising 1 to 8 substituted or unsubstituted methine radicals; and $Y^\ominus$ is an acid radical.

Typical examples of the aromatic rings represented by $A^1$ and $A^2$ are furan, thiophene, imidazole, pyrrole, 1,6-diazanaphthalene, 1,7-diazanaphthalene, 1,5-diazanaphthalene, pyridine, 1,2-diazine, 1,3-diazine, 1,4-diazine, quinoline, isoquinoline, quinoxaline, 1,3-benzodiazine and 2,3-benzodiazine, as well as a condensed ring of two or more of these aromatic rings.

Examples of the alkyl group represented by $R^1$ to $R^7$ are alkyl groups of 1 to 12 carbon atoms such as methyl, ethyl, n-propyl, iso-propyl, n-butyl, sec-butyl, iso-butyl, t-butyl, n-amyl, t-amyl, n-hexyl, n-octyl, and t-octyl, and above all, straight-chain or branched alkyl groups of 1 to 4 carbon atoms are preferable.

Examples of the substituted alkyl group are 2-hydroxyethyl, 2-methoxyethyl, 2-ethoxyethyl, 3-hydroxypropyl, 3-methoxypropyl, 3-ethoxypropyl, 3-chloropropyl, 3-bromopropyl and 3-carboxypropyl.

Examples of the alkoxy group are groups having the same carbon numbers and the same structures as in the case of the alkyl group, such as methoxy, ethoxy, propoxy, ethoxyethyl and methoxymethyl.

Examples of the substituted or unsubstituted aryl group are phenyl, tolyl, xylyl, biphenyl, aminophenyl, α-naphthyl, β-naphthyl, anthranyl, pyrenyl, methoxyphenyl, dimethoxyphenyl, trimethoxyphenyl, ethoxyphenyl, diethoxyphenyl, chlorophenyl, dichlorophenyl, trichlorophenyl, bromophenyl, dibromophenyl, tribromophenyl, ethylphenyl, diethylphenyl, nitrophenyl, aminophenyl, dimethylaminophenyl, diethylaminophenyl, dibenzylaminophenyl, dipropylaminophenyl, morpholinophenyl, piperidinylphenyl, piperazinophenyl, diphenylaminophenyl, acetylaminophenyl, benzoylaminophenyl, acetylphenyl, benzoylphenyl, cyanophenyl, sulfonated phenyl and carboxylated phenyl.

Preferable examples of the substituted or unsubstituted amino group are amino groups having 10 or less carbon atoms, such as amino, dimethylamino, diethylamino, dipropylamino, acetylamino and benzoylamino.

Examples of the substituted or unsubstituted aralkyl group are aralkyl groups of 7 to 19 carbon atoms, preferably of 7 to 15 carbon atoms, such as benzyl, phenethyl, tolylmethyl, hydroxybenzyl, 2-hydroxy-3-methylbenzyl and 2-hydroxy-3-t-butylbenzyl.

The compound represented by the general formula (I) is usually sparingly soluble in water, and therefore, in order to impart water-soluble properties to the compound, one or more of $R^1$ to $R^7$ preferably contain a polar group. Examples of the polar groups are conventional groups such as hydroxyl, an alkylhydoxyl group, a sulfonate group, an alkylsulfonate group, a carboxylate group, an alkylcarboxylate group and a tert-ammonium salt. However, if it is confirmed that the water-solubility of the labeled nucleic acid probe is water-soluble, the label compound need not to be always water-soluble and the introduction of the polar group is unnecessary.

$R^1$ to $R^7$ preferably contain one or more reactive groups so that the compound of the general formula (I) may form a covalent bond with the nucleic acid probe. However, when the compound of the general formula (I) is intercalated into the nucleic acid probe, or if the labeling by ionic bonding is possible, the reactive group is not always necessary.

Examples of the reactive group are known groups having a reactive site, such as isocyanate, isothiocyanate, succinimido ester, sulfosuccinimido ester, imido ester, hydrazine, nitroaryl halides, bipyridine disulfide, maleimide, thiophthalimide, acid halides, sulfonyl halides, aziridine, azidonitrophenyl, azidoamino and 3-(2-pyridyldithio) propionamide. In order to prevent the steric hindrance attributed to the bonding of the label compound to the nucleic acid probe, a spacer such as

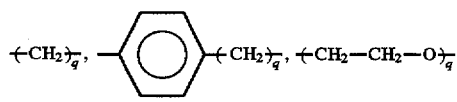

(wherein q is 0 or an integer of 1 to 6) may be introduced into the reactive group.

Particularly preferable examples of the abovementioned reactive groups are isothiocyanate, sulfosuccinimide ester, succinimide ester and maleimide.

Next, examples of the methine chain represented by L are the following groups

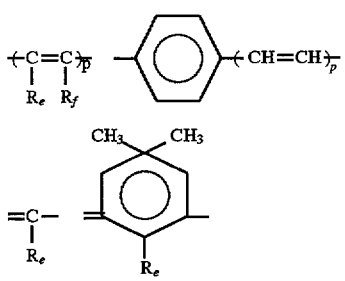

wherein $R_e$ and $R_f$ are each independently a hydrogen atom or a substituent, and examples of this substituent include an alkyl group, halogen atoms such as I, Br and Cl, an alkoxy group, an aryl group, an aralkyl group, an alkyl sulfonate group and an alkenyl group; and p is an integer of 0, 1, 2 or 3.

Examples of the acid radical represented by $Y^{\ominus}$ are chloride ion, bromide ion, iodide ion, perchlorate ion, benzene sulfonate ion, p-toluene sulfonate ion, methyl sulfate ion, ethyl sulfate ion, propyl sulfate ion, tetrafluoroborate ion, tetraphenyl borate ion, hexafluorophosphate ion, benzene sulfinate ion, acetate ion, trifluoroacetate ion, propionate ion, benzoate ion, oxalate ion, succinate ion, malonate ion, oleate ion, stearate ion, citrate ion, monohydrogen diphosphate ion, dihydrogen monophosphate ion, pentachlorostannate ion, chlorosulfate ion, fluorosulfonate-ion, trifluoromethane sulfonate ion, hexafluoroantimonate ion, molybdate ion, tungstate ion, titanate ion and zirconate ion.

Typical examples of the cyanine dyes are as follows:

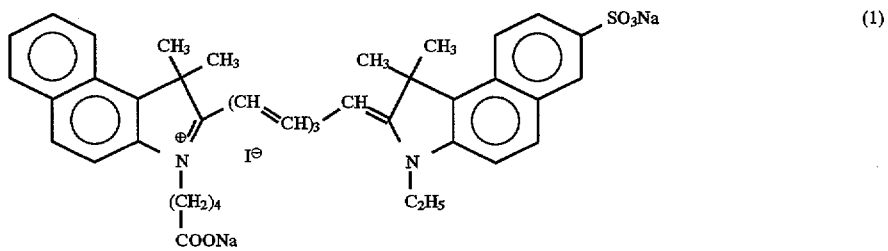

(1)

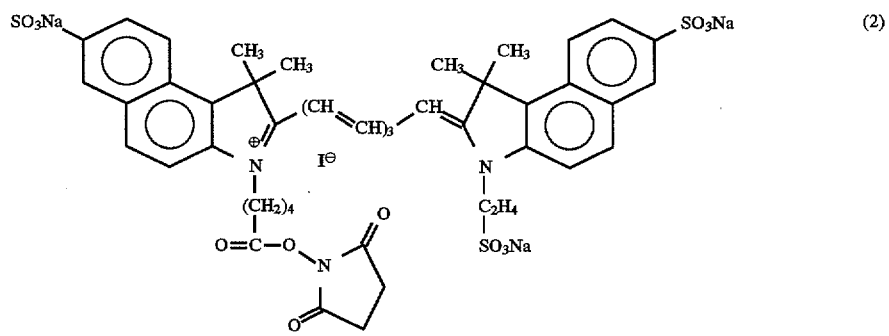

(2)

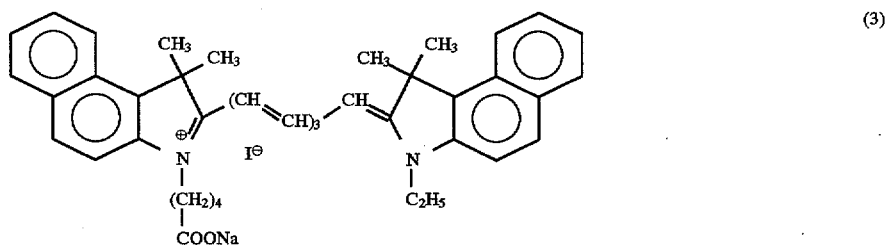

(3)

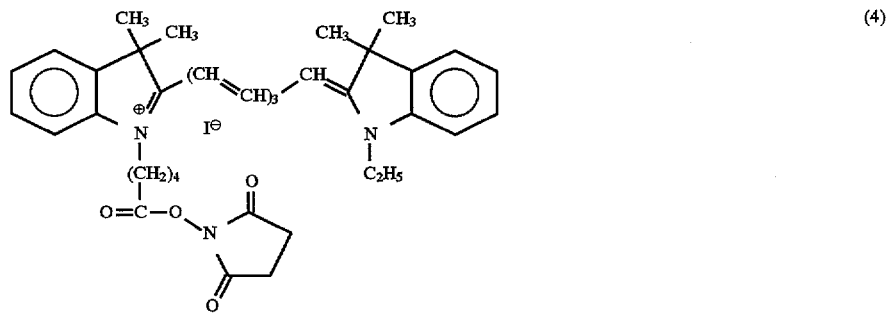

(4)

-continued
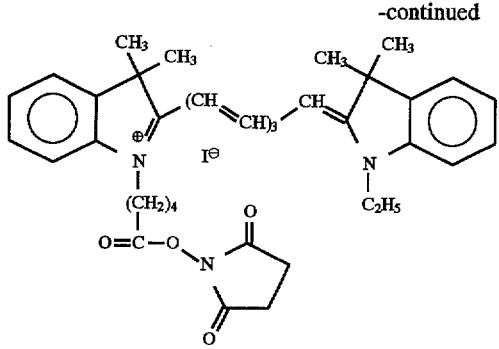
(5)
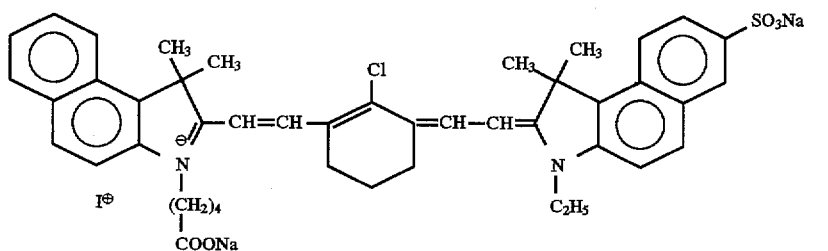
(6)
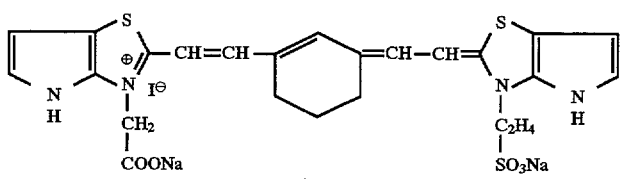
(7)
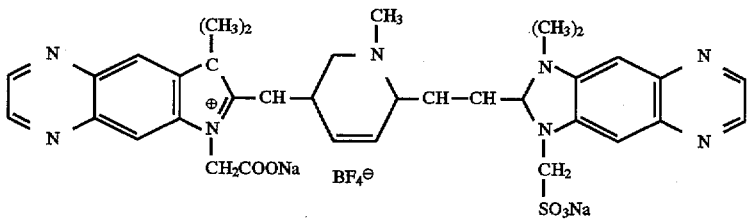
(8)
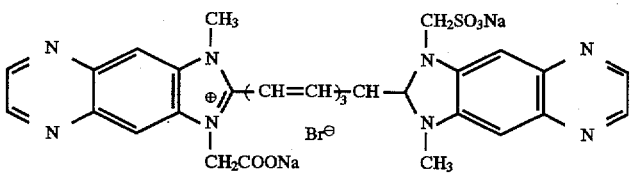
(9)
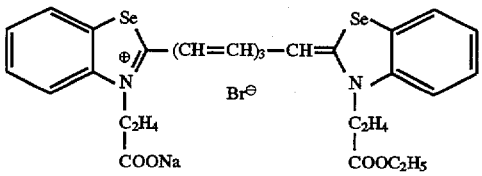
(10)

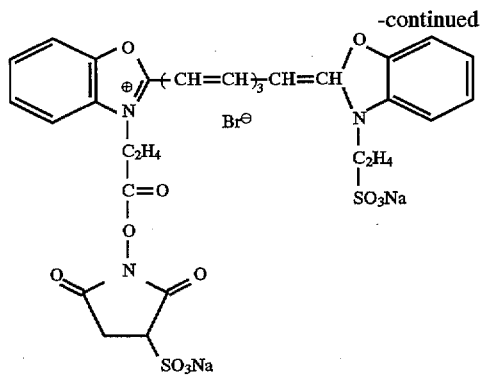

(11)

In the present invention, the preferable trinuclear type dye are those having a structure in which three aromatic heterocycles linked with each other by at least one (poly)methine chain [the following general formula (II)] and salts thereof [the following general formula (III)]:

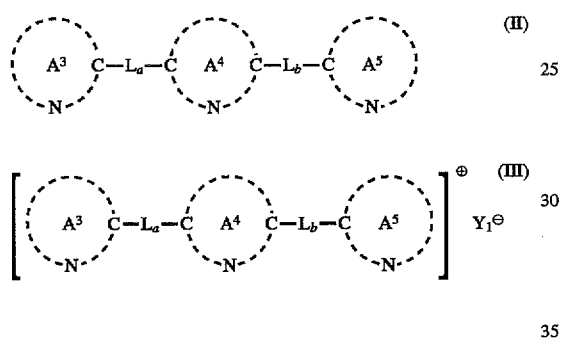

wherein $A^3$, $A^4$ and $A^5$ are each a substituted or unsubstituted five-membered or six-membered aromatic heterocycle having at least one or two nitrogen atoms, or a condensed ring containing such a heterocycle; $L_a$ and $L_b$ are each a methine chain comprising 1 to 6 substituted or unsubstituted methine radicals, and one of $L_a$ and $L_b$ may be omitted, so that the aromatic heterocycles are directly bonded to each other; and $Y_1^\ominus$ is an acid radical.

Examples of the substituted and unsubstituted five-membered and six-membered aromatic heterocycles containing nitrogen atom(s) are as follows:

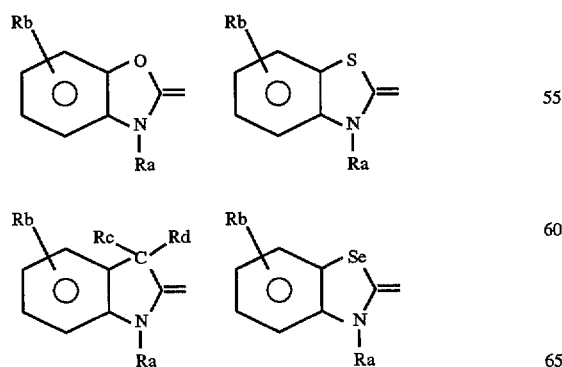

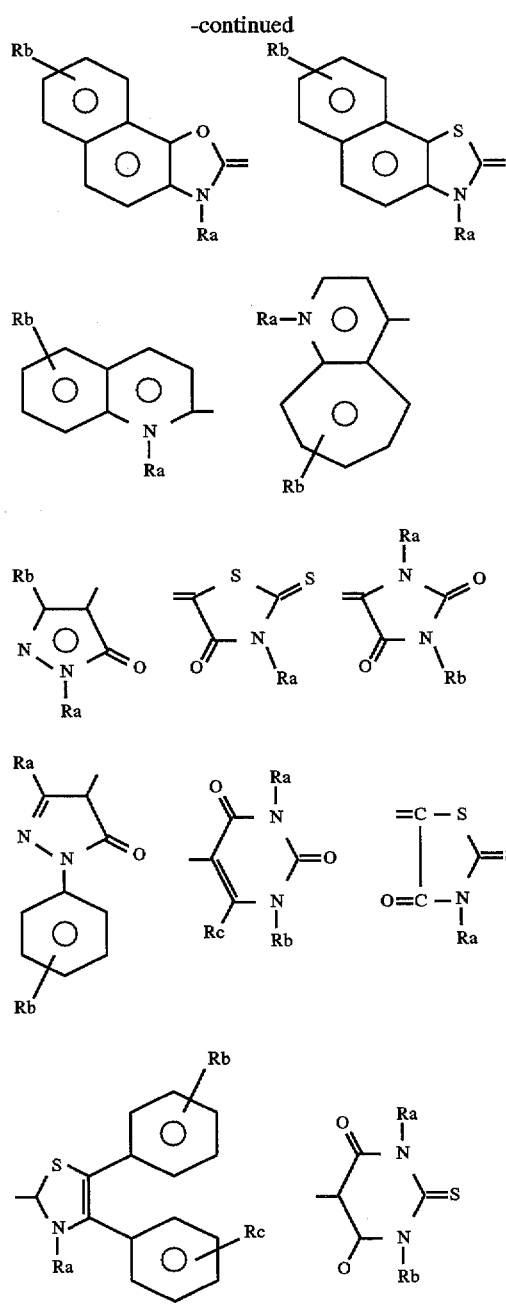

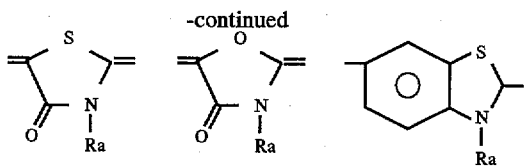

(wherein Ra, Rb, Rc and Rd are each independently a hydrogen atom or a substituent).

Examples of this substituent are an alkyl group, a halogen such as I, Br and Cl, an alkoxy group, an alkyl sulfonate group and an alkenyl group.

The aromatic heterocycle does not include a cycle merely formed by bridging two or more carbon atoms of the polymethine chain. That is to say, such a cycle is usually a carbon ring, and such a structure does not contribute to the increase in Stokes' shift.

The tri-aromatic heterocycles constituting the trinuclear type dye are linked with each other by the methine chains represented by $L_a$ and $L_b$, comprising 1 to 6 substituted or unsubstituted methine radicals (when only one methine radical is present, the aromatic heterocycles are linked by a carbon atom instead of a methine chain, but for convenience, it is also called a methine chain), so that a resonance system is formed within the tri-aromatic heterocycles. One of $L_a$ and $L_b$ may be omitted, so that the two aromatic heterocycles are directly linked to each other. The number of methine radicals may be odd or even. In the case of the even number, bonding between the methine radicals and the aromatic heterocycles are either a single bond or a double bond, but in the case of the odd number, they are linked by a single bond and a double bond respectively. A preferable unit of the methine chain comprises two methine radicals having double bonds at the both ends thereof. The number of the repeating unit is 3 or less, and in other words, the number of the methine radicals is 6 or less. If the methine chain is longer than this number, absorption wavelength excessively shifts to 900 nm or more and the compound itself also becomes unstable. When neither $L_a$ nor $L_b$ is present, the aromatic heterocycles are directly linked, and the absorption wavelength inconveniently becomes shorter than 600 nm.

Next, $L_a$ and $L_b$ are exemplified below.

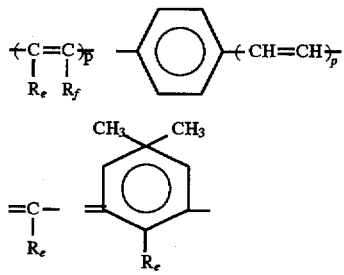

wherein $R_e$ and $R_f$ are each an aryl group, an aralkyl group or a group represented by $R_a$ to $R_d$; and p is an integer of 0, 1, 2 or 3.

The compound represented by the general formula (II) may be an ionized salt form represented by the general formula (III). This salt is used when an ionic interaction like an ionic bonding with a biomaterial is desirable. In the general formula (III), $Y_1^{\ominus}$ is an acid radical. Examples of this acid radical are the same acid radicals as in the general formula (I).

Typical examples of the thus constituted trinuclear type dye are trinuclear type cyanine dyes, trinuclear type mero-cyanine dyes, trinuclear type rhodacyanine dyes, trinuclear type oxonol dyes, trinuclear type styryl dyes and trinuclear type basic styryl dyes.

A more preferable trinuclear type dye is a compound represented by the general formula (V) or an isomer thereof having a nitrogen atom at 5-position of the middle heterocycle of the general formula (V) instead of at 4-position thereof:

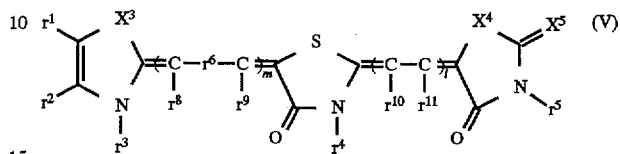

wherein $r^8$, $r^9$, $r^{10}$ and $r^{11}$ are each independently a hydrogen atom, a halogen atom, a substituted or unsubstituted alkyl group, an alkoxy group, a substituted or unsubstituted aryl group, or a substituted or unsubstituted amino group, and $r^8$ and $r^9$ may be bonded together to form a substituted or unsubstituted aromatic ring; $r^6$ is not present in a repeating unit or an alkyl-substituted ethylene, and $r^6$ may be bonded to $r^8$ or $r^9$ to form a ring structure; $r^1$ and $r^2$ are each a substituted or unsubstituted aryl group, or $r^1$ and $r^2$ may together form a substituted or unsubstituted condensed ring; $r^3$, $r^4$ and $r^5$ are each independently a hydrogen atom, a substituted or unsubstituted alkyl group, an alkylsulfonate group, an alkenyl group, a substituted or unsubstituted aryl group, or a substituted or unsubstituted aralkyl group; $X^3$ is an oxygen atom, a sulfur atom, a carbon atom, a nitrogen atom or a selenium atom, and in the case that $X^3$ is a carbon atom or a nitrogen atom, this group binds to a hydrogen atom, a substituted or unsubstituted alkyl group, a substituted or unsubstituted aryl group, or a substituted or unsubstituted aralkyl group; $X^4$ is an oxygen atom, a sulfur atom or a nitrogen atom, and in the case that $X^4$ is a nitrogen atom, any of a hydrogen atom, a substituted or unsubstituted alkyl group, a substituted or unsubstituted aryl group, or a substituted and unsubstituted aralkyl group may bind to it; $X^5$ is an oxygen atom or a sulfur atom; and m and l are each an integer of 0 to 3, and either of them is not 0.

Another trinuclear type dye is a compound represented by the following general formula (VI) or an isomer thereof having a nitrogen atom at 5-position of the middle heterocycle of the general formula (V) instead of at 4-position thereof:

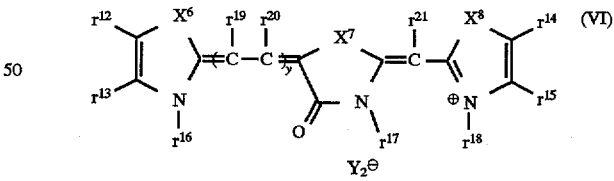

wherein $r^{19}$, $r^{20}$ and $r^{21}$ are each independently a hydrogen atom, a halogen atom, a substituted or unsubstituted alkyl group, an alkoxy group, a substituted or unsubstituted aryl group, or a substituted or unsubstituted amino group, and $r^{19}$ and $r^{20}$ may be bonded to each other to form a substituted or unsubstituted condensed ring; $r^{12}$, $r^{13}$, $r^{14}$ and $r^{15}$ are each a substituted or unsubstituted aryl group, or $r^{12}$ and $r^{13}$ or $r^{14}$ and $r^{15}$ may be bonded to each other to form a substituted or unsubstituted condensed ring; $r^{16}$, $r^{17}$ and $r^{18}$ are each independently a hydrogen atom, a substituted or unsubstituted alkyl group, an alkylsulfonate group, an alkenyl group, a substituted or unsubstituted aryl group, or a substituted or unsubstituted aralkyl group; $X^6$ and $X^8$ are each independently an oxygen atom, a sulfur atom, a carbon atom, a nitrogen atom or a selenium atom, and in the case that $X^6$ and $X^8$ are each the carbon atom or the nitrogen atom, these groups bond to any of a hydrogen atom, a substituted or unsubstituted alkyl group, a substituted or unsubstituted aryl group, or a substituted or unsubstituted aralkyl group; $X^7$ is an oxygen atom, a sulfur atom or a nitrogen atom, and in the case that $X^7$ is the nitrogen atom, this group bonds to any of a hydrogen atom, a substituted or unsubstituted alkyl group, a substituted or unsubstituted aryl group, or a substituted or unsubstituted aralkyl group; $Y_2^\ominus$ is an acid radical including the same acid radicals as in the general formula (I); and y is an integer of 0, 1 or 2.

Preferable examples of the trinuclear type dye are the compounds represented by the general formulae (V) and (VI), but the trinuclear type dye of the general formula (V) is particularly preferable.

Examples of the alkyl groups in the general formula (V) or (VI) are alkyl groups of 1 to 12 carbon atoms, preferably straight-chain or branched alkyl groups having 1 to 4 carbon atoms, such as methyl, ethyl, n-propyl, iso-propyl, n-butyl, sec-butyl, iso-butyl, t-butyl, n-amyl, t-amyl, n-hexyl, n-octyl, and t-octyl.

Examples of the substituted alkyl group include 2-hydroxyethyl, 2-methoxyethyl, 2-ethoxyethyl, 3-hydroxypropyl, 3-methoxypropyl, 3-ethoxypropyl, 3-chloropropyl, 3-bromopropyl and 3-carboxypropyl.

Examples of the alkoxy group include groups having the same carbon numbers and the same structures as in the case of the alkyl group, such as methoxy, ethoxy, propoxy ethoxyethyl and methoxymethyl.

Examples of the substituted or unsubstituted aryl group are phenyl, tolyl, xylyl, biphenyl, aminophenyl, α-naphthyl, β-naphthyl, anthranyl, pyrenyl, methoxyphenyl, dimethoxyphenyl, trimethoxyphenyl, ethoxyphenyl, diethoxyphenyl, chlorophenyl, dichlorophenyl, trichlorophenyl, bromophenyl, dibromophenyl, tribromophenyl, ethylphenyl, diethylphenyl, nitrophenyl, aminophenyl, dimethylaminophenyl, diethylaminophenyl, dibenzylaminophenyl, dipropylaminophenyl, morpholinophenyl, piperidinylphenyl, piperazinophenyl, diphenylaminophenyl, acetylaminophenyl, benzoylaminophenyl, acetylphenyl, benzoylphenyl, cyanophenyl, sulfonated phenyl and carboxylated phenyl.

Examples of the alkenyl group are alkenyl groups of 1 to 10 carbon atoms, preferably 1 to 6 carbon atoms, such as vinyl, propenyl, butenyl, pentenyl, hexenyl, heptenyl, octenyl and dodecynyl.

Examples of the substituted or unsubstituted aralkyl group are aralkyl groups having 7 to 19 carbon atoms, preferably 7 to 15 carbon atoms, such as benzyl, phenethyl, tolylmethyl, hydroxybenzyl, 2-hydroxy-3-methylbenzyl and 2-hydroxy-3-t-butylbenzyl.

The label compound represented by the general formula (V) or (VI) is usually sparingly soluble in water, and therefore, in order to impart water-soluble properties to the compound, one or more of $r^1$ to $r^{21}$ preferably contain polar groups. Examples of the polar groups are known groups such as hydroxyl, an alkylhydoxyl group, a sulfonate group, an alkylsulfonate group, a carboxylate group, an alkylcarboxylate group and a tert-ammonium salt. However, if it is confirmed that the water-solubility of the labeled nucleic acid probe is water-soluble, the label compound need not to be always water-soluble and the introduction of the polar group is unnecessary.

Preferably, $r^1$ to $r^5$ or $r^{12}$ to $r^{15}$ contain one or more reactive groups so that the compound of the general formula (V) or (VI) may form a covalent bond with the nucleic acid probe. However, if the compound of the general formula (V) or (VI) is intercalated into the nucleic acid probe, or if the labeling by ionic bonding or the like is possible, the reactive group is not always necessary.

Examples of the reactive group are known groups having a reactive site, such as isocyanate, isothiocyanate, succinimido ester, sulfosuccinimido ester, imido ester, hydrazine, nitroaryl halides, bipyridine disulfide, maleimide, thiophthalimide, acid halides, sulfonyl halides, aziridine, azidonitrophenyl, azidoamino and 3-(2-pyridyldithio) propionamide. In order to prevent the steric hindrance attributed to the bonding of the label compound to the nucleic acid probe, a spacer such as

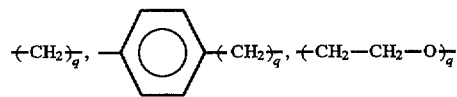

(wherein q is 0 or an integer of 1 to 6) may be introduced into the reactive group.

Particularly preferable examples of the reactive group are isocyanate, sulfosuccinimido ester, succinimido ester and maleimide.

Typical examples of the trinuclear type dye are as follows:

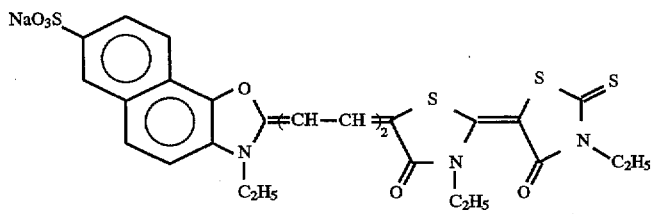

(1)

-continued
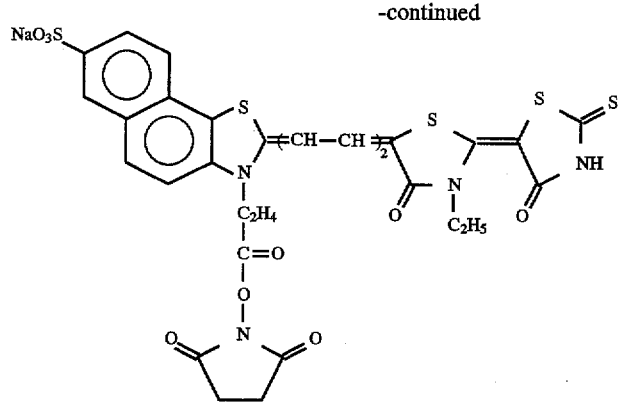
(2)
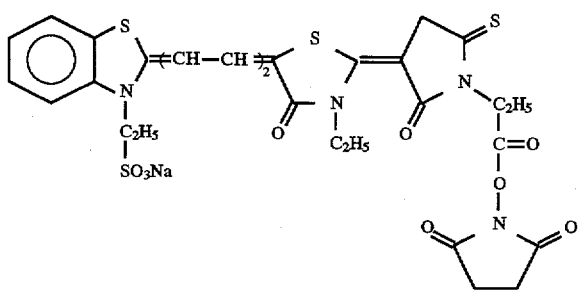
(3)
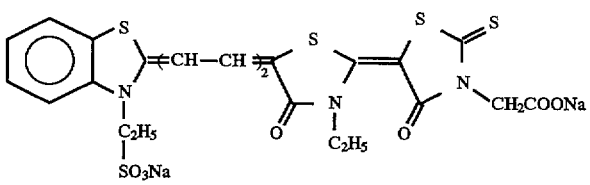
(4)
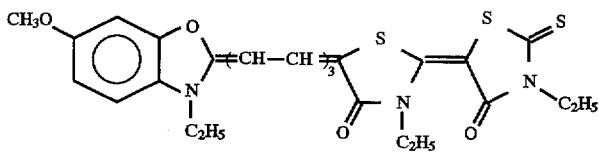
(5)
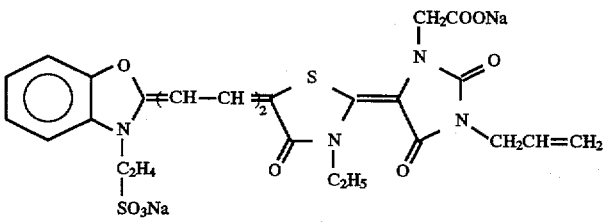
(6)
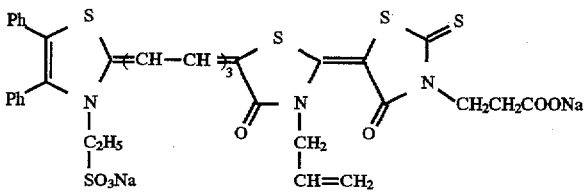
(7)
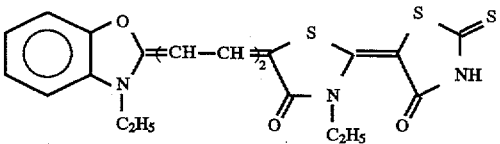
(8)

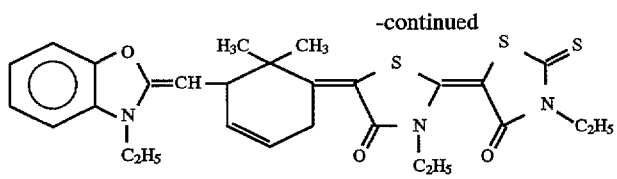

(9)

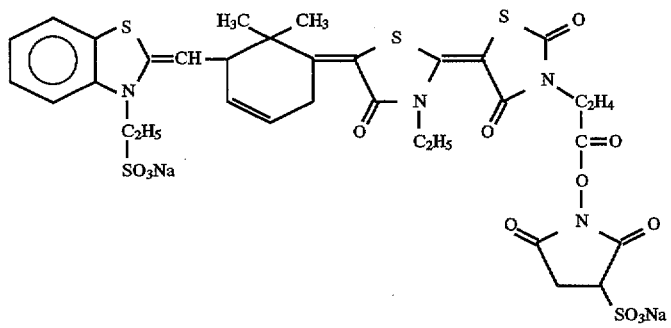

(10)

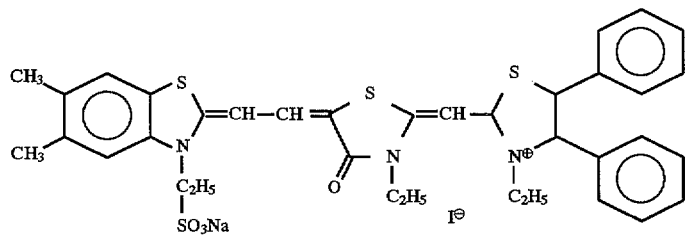

(11)

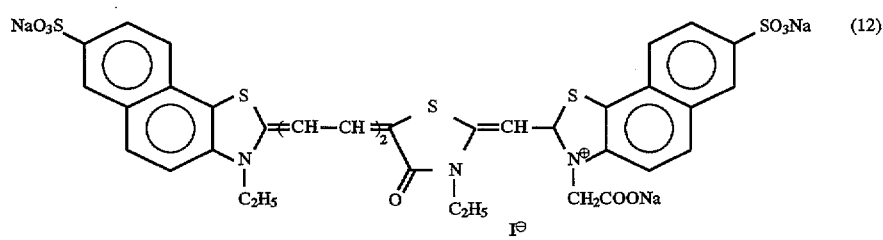

(12)

The azulene dye which can be used in the present invention is represented by the general formula (IV):

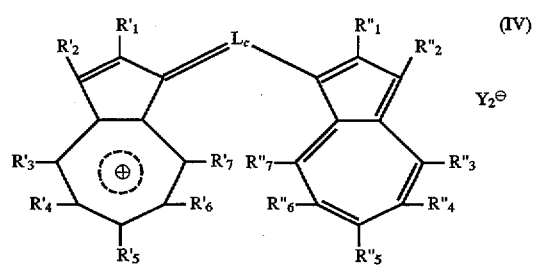

(IV)

wherein $R'_1$ to $R'_7$ and $R''_1$ to $R''_7$ are each independently a hydrogen atom, a halogen atom, a substituted or unsubstituted alkyl group, an alkoxy group, a substituted or unsubstituted aryl group, an alkenyl group, a substituted or unsubstituted aralkyl group, a substituted or unsubstituted styryl group, an arylazo group, a sulfonate group, an amino group, a nitro group, a hydroxyl group, a carboxyl group or a cyano group, and $R'_1$ to $R'_7$ or $R''_1$ to $R''_7$ may be bonded to each other to form a substituted or unsubstituted condensed ring; $Y_2^{\ominus}$ is an anion; and $L_c$ is a methine chain comprising 1 to 8 substituted or unsubstituted methine radicals.

Examples of the alkyl group represented by $R'_1$ to $R'_7$ and $R''_1$ to $R''_7$ are alkyl groups having 1 to 12 carbon atoms, such as methyl, ethyl, n-propyl, iso-propyl, n-butyl, sec-butyl, iso-butyl, t-butyl, n-amyl, t-amyl, n-hexyl, n-octyl, and t-octyl, especially straight-chain or branched alkyl groups of 1 to 4 carbon atoms are preferable.

Examples of the substituted alkyl group are 2-hydroxyethyl, 2-methoxyethyl, 2-ethoxyethyl, 3-hydroxypropyl, 3-methoxypropyl, 3-ethoxypropyl, 3-chloropropyl, 3-bromopropyl and 3-carboxypropyl. Furthermore, examples of the alkoxy group include methoxy, ethoxy, propoxy, ethoxyethyl and methoxyethyl.

Examples of the alkoxy group are those having the same carbon numbers and the same structures as in the case of the alkyl group, such as methoxy, ethoxy, propoxy and ethoxyethyl.

Examples of the substituted or unsubstituted aryl group are phenyl, tolyl, xylyl, biphenyl, aminophenyl, α-naphthyl, β-naphthyl, anthranyl, pyrenyl, methoxyphenyl, dimethoxyphenyl, trimethoxyphenyl, ethoxyphenyl, diethoxyphenyl, chlorophenyl, dichlorophenyl, trichlorophenyl, bromophenyl, dibromophenyl, tribromophenyl, ethylphenyl, diethylphenyl, nitrophenyl, aminophenyl, dimethylaminophenyl, diethylaminophenyl, dibenzylaminophenyl, dipropylaminophenyl, morpholinophenyl, piperidinylphenyl, piperazinophenyl, diphenylaminophenyl, acetylaminophenyl, benzoylaminophenyl, acetylphenyl, benzoylphenyl, cyanophenyl, sulfonated phenyl and carboxylated phenyl.

Examples of the alkenyl group are alkenyl groups having 1 to 10 carbon atoms, preferably 1 to 6 carbon atoms, such as vinyl, propenyl, butenyl, pentenyl, hexenyl, heptenyl, octenyl and dodecynyl.

Preferable examples of the substituted or unsubstituted aralkyl group are aralkyl groups having 7 to 19 carbon atoms, preferably 7 to 15 carbon atoms, such as benzyl, phenethyl, tolylmethyl, hydroxybenzyl, 2-hydroxy-3-methylbenzyl and 2-hydroxy-3-t-butylbenzyl.

Preferable examples of the substituted or unsubstituted amino group are amino groups having 10 or less carbon atoms, such as amino, dimethylamino, diethylamino, dipropylamino, acetylamino and benzoylamino.

Preferable examples of the substituted or unsubstituted styryl group are styryl groups having 8 to 14 carbon atoms, such as styryl, dimethylaminostyryl, diethylaminostyryl, dipropylaminostyryl, methoxystyryl, ethoxystyryl and methylstyryl.

Examples of the arylazo group are arylazo groups having 8 to 14 carbon atoms, such as phenylazo, α-naphthylazo, η-naphthylazo, dimethylaminophenylazo, chlorophenylazo, nitrophenylazo and methoxyphenylazo.

In the general formula (IV), at least one of combinations of $R'_1$ and $R'_2$, $R'_2$ and $R'_3$, $R'_3$ and $R'_4$, $R'_4$ and $R'_5$, $R'_5$ and $R'_6$, and $R'_6$ and $R'_7$ may form a substituted or unsubstituted condensed ring. This condensed ring is a five-membered, a six-membered or a seven-membered condensed ring, and examples of the condensed ring are aromatic rings (such as benzene, naphthalene, chlorobenzene, bromobenzene, methylbenzene, ethylbenzene, methoxybenzene and ethoxybenzene), heterocyclic rings (such as furan, benzofuran, pyrrole, thiophene, pyridine, quinoline and thiazole), and aliphatic rings (such as dimethylene, trimethylene and tetramethylene).

The compound represented by the general formula (IV) is usually sparingly soluble in water, and therefore, in order to impart water-soluble properties to the label compound, one or more of $R'_1$ to $R'_7$ and $R''_1$ to $R''_7$ preferably contain known polar groups. Examples of the polar groups are hydroxyl, an alkylhydoxyl group, a sulfonate group, an alkylsulfonate group, a carboxylate group, an alkylcarboxylate group and a tert-ammonium base. However, if it is confirmed that the water-solubility of the labeled nucleic acid probe is water-soluble, the label compound need not to be always water-soluble and the introduction of the polar group is unnecessary.

Moreover, $R'_1$ to $R'_7$ and $R''_1$ to $R''_7$ preferably contain one or more reactive groups so that the compound of the general formula (IV) may form a covalent bond with the nucleic acid probe. However, if the compound of the general formula (V) or (VI) is intercalated into the nucleic acid probe, or if the labeling by ionic bonding or the like is possible, the reactive group is not always necessary.

Examples of the reactive group include groups having a reactive site, such as isocyanate, isothiocyanate, succinimido ester, sulfosuccinimido ester, imido ester, hydrazine, nitroaryl halides, bipyridine disulfide, maleimide, thiophthalimide, acid halides, sulfonyl halides, aziridine, azidonitrophenyl, azidoamino and 3-(2-pyridyldithio) propionamide. In order to prevent the steric hindrance attributed to the bonding of the label compound to the nucleic acid probe, a spacer such as

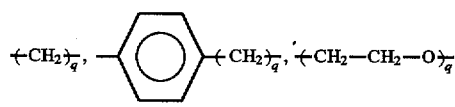

(wherein q is 0 or an integer of 1 to 6) may be introduced into the reactive group.

Particularly preferable examples of the above-mentioned reactive groups include isothiocyanate, sulfosuccinimido ester, succinimido ester and maleimide.

Next, examples of the methine chain represented by $L_c$ are the following groups

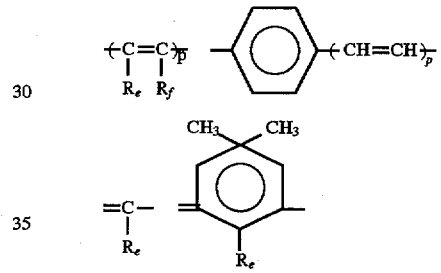

wherein $R_e$ and $R_f$ are each independently a hydrogen atom or a substituent, and examples of this substituent are an alkyl group, a halogen such as I, Br and Cl, an alkoxy group, an aryl group, an aralkyl group, an alkyl sulfonate group and an alkenyl group; and p is an integer of 0, 1, 2 or 3.

Examples of the acid radical represented by $Y_2^\ominus$ are the same groups as mentioned in the case of $Y^\ominus$.

Typical examples of the azulene dyes are as follows:

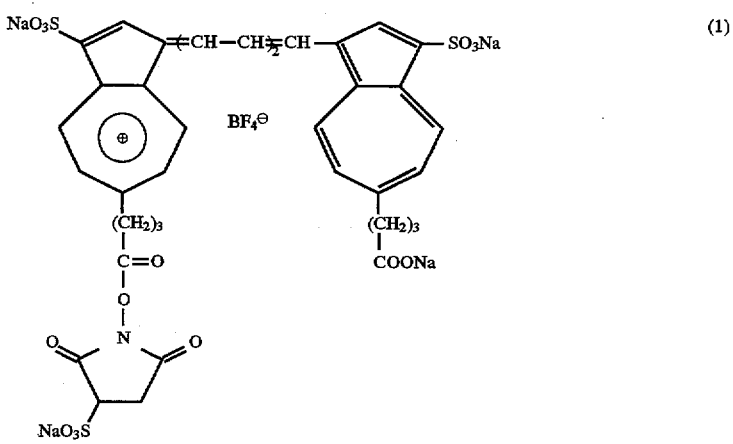

(1)

-continued
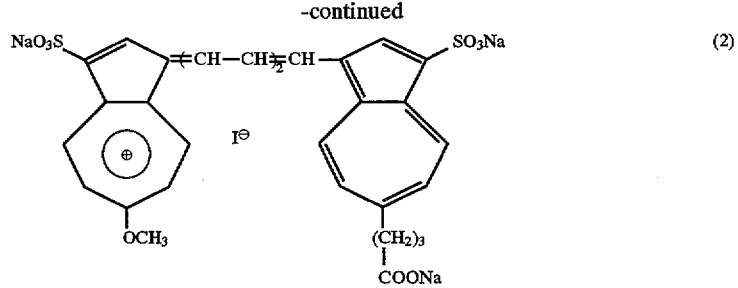 (2)
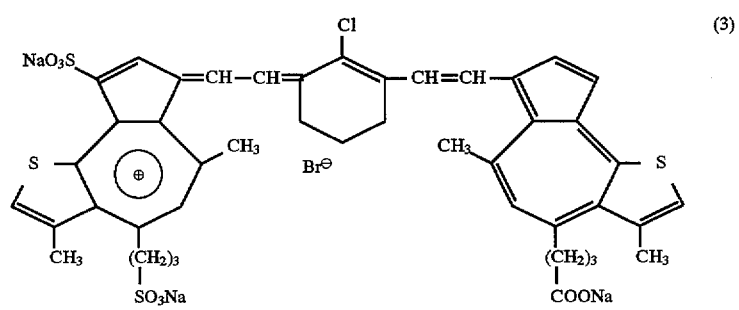 (3)
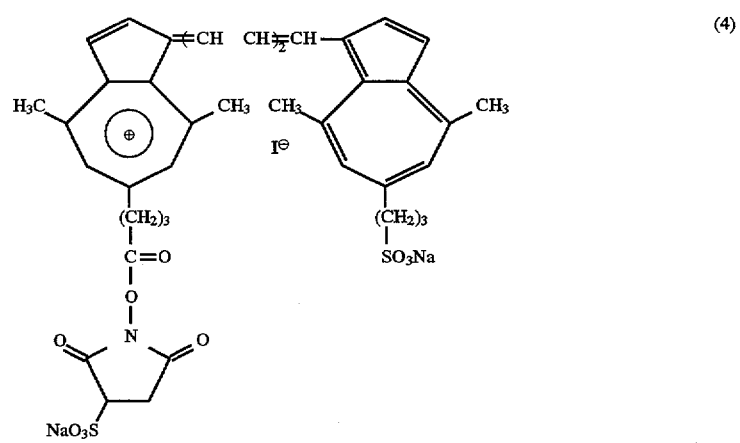 (4)
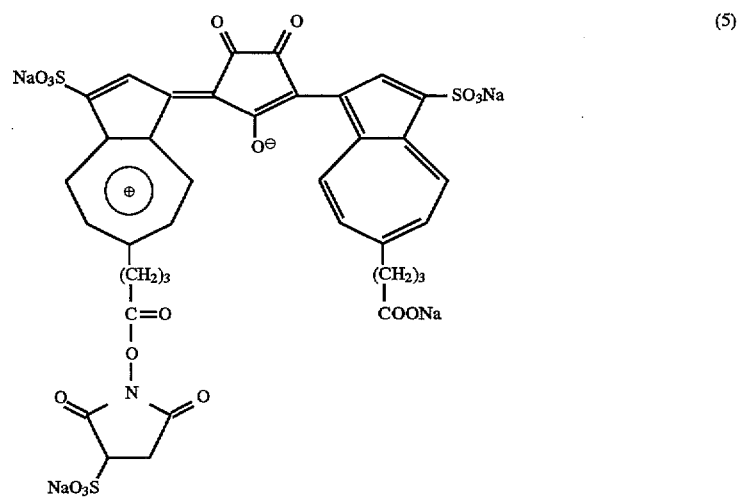 (5)

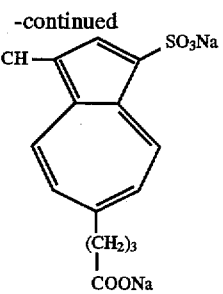

(6)

The employment of the cyanine dye, the trinuclear type dye or the azulene dye to label the nucleic acid probe permits the use of an inexpensive gas laser or semiconductor laser as a light source for label detection, and the selection of the suitable label for the probe from these dyes also permits the simultaneous measurement at multi-wavelength.

With regard to the previously mentioned commercially available cyanine dye Cy-5, the absorption maximum is at 652 nm and the fluorescence maximum is at 667 nm, not in the wavelength range to which the above-mentioned semiconductor laser can be applied. In addition, its Stokes' shift is as small as 15 nm, and this value is far apart from the above-mentioned 40 to 50 nm which are considered to be useful in the present invention.

The cyanine dyes and the azulene dyes have been extensively studied. As described above, Japanese Patent Application No. 4-15665 mentions a nucleic acid probe labeled with an azulene-based fluorescent dye, and Japanese Patent Application No. 1-171326 mentions a nucleic acid probe labeled with a cyanine-based fluorescent dye. In these publications, however, the characteristics of these probes in capillary electrophoresis have not been evaluated, and in Japanese Patent Application No. 1-171326, there is no synthetic example of the cyanine-based fluorescent dye which can be excited by the semiconductor laser at 780 nm.

In point of the Stokes' shift which is concerned with the improvement of an S/N ratio of fluorescent signals, the trinuclear type dye and the azulene dye are more preferable than the cyanine dye, because the Stokes' shifts of the trinuclear type dye and the azulene dye are as large as about 50 nm or more.

The reasons why the cyanine dye, the trinuclear type dye and the azulene dye in the present invention are desirable as the fluorescent label compound for the nucleic acid probe to be used in capillary electrophoresis are as follows.

(1) Usually when the target nucleic acid is detected using a nucleic acid probe, this nucleic acid probe is exposed to high temperature only during the hybridization reaction, and the temperature rise is prevented during electrophoresis by controlling voltage etc. In capillary electrophoresis, however, a long capillary having an extremely small inner diameter is used and it is impossible to reduce the voltage as in the case of usual slab gel electrophoresis. Therefore, the temperature in the capillary rises inevitably. When the hybrid double-strand nucleic acid is subjected to electrophoresis, the temperature in the capillary must be regulated, in principle, not to rise to or over the melting point of the double-strand nucleic acid, so that the temperature in the capillary is controlled from the outside. However, it is sometimes inevitable that the temperature in the capillary stays at a high temperature of 60° C. or more for a long period of time, depending upon the state of separation, the distance of the electrophoresis, the chain length of the nucleic acid probe and the like. As with the ordinary fluorescent dyes having absorption and fluorescence at 600 nm or more, for example, in the case of a Rhodamine dye, there is a problem that this dye cannot withstand the high temperature conditions resulting in color fade.

On the contrary, the cyanine dye, the trinuclear type dye and the azulene dye which can be used in the present invention are stable under the above-mentioned temperature conditions, and even if the temperature in the capillary rises, there does not occur the problem of the color failure.

(2) The capillary used in capillary electrophoresis is usually made of glass. The present inventors have examined the adsorption ability to glass, of Rhodamine dye which is a common fluorescent dye, and the cyanine dye, the trinuclear type dye and the azulene dye which can be used in the present invention. As a result, it is apparent that the Rhodamine dye tends to adsorb on the glass, whereas the cyanine dye and the azulene dye scarcely adsorb on the glass. In the case of capillary electrophoresis, a trace amount of the nucleic acid is used, and so it is very important that the label compound bound to the nucleic acid probe does not adsorb on the glass.

(3) In capillary electrophoresis, a high voltage is applied to the glass capillary having an extremely small inner diameter, and the charging state and pH locally fluctuate in the capillary, particularly on the inner surface. It is well known that the structure or the optical characteristics such as absorption properties and fluorescent properties of dyes will change in response to the change of pH.

The cyanine dye, the trinuclear type dye and the azulene dye according to the present invention are more stable in the pH range of 4.5 to 9.0 which covers the pH in the capillary, as compared with the Rhodamine dye, a common fluorescent dye.

Next, the present invention will be explained in more detail with regard to examples. However, the scope of the present invention should not be limited to these examples.

Compounds Nos. 1 to 12 which will be used in the following examples have the following structures.

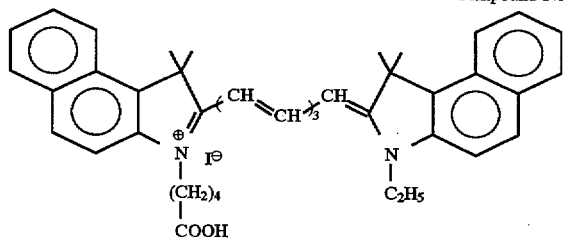

Compound No. 1

Compound No. 2

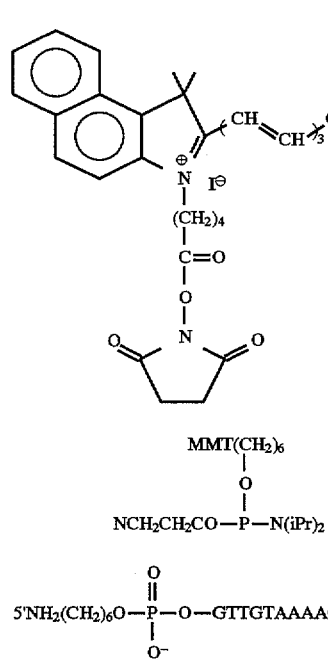

Compound No. 3

MMT(CH₂)₆
         |
         O
         |
NCH₂CH₂CO—P—N(iPr)₂

Compound No. 4

$$5'NH_2(CH_2)_6O-\overset{\overset{O}{\|}}{\underset{\underset{O^-}{|}}{P}}-O-GTTGTAAAACGACGGCCAGT3'$$

(The nucleotide portion of Compound No. 4 is shown in SEQ ID NO:1.)

Compound No. 5

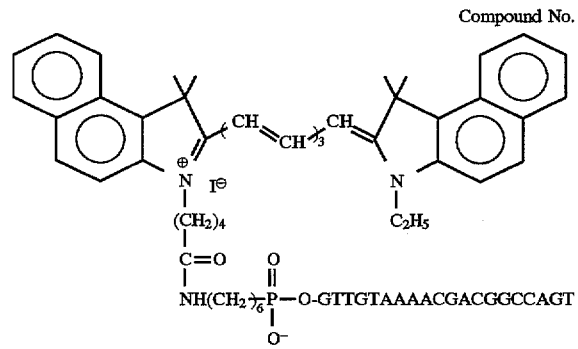

(The nucleotide portion of Compound No. 5 is shown in SEQ ID NO:1.)

Compound No. 6

5'ACTGGCCGTCGTTTTACAAC 3'  (SEQ ID NO:2.)

Compound No. 7

5'ACTGGCCGTCCTTTTACAAC 3'  (SEQ ID NO:3.)

Compound No. 8

5'ACTGGCGGTCGTTATACAAC 3'  (SEQ ID NO:4.)

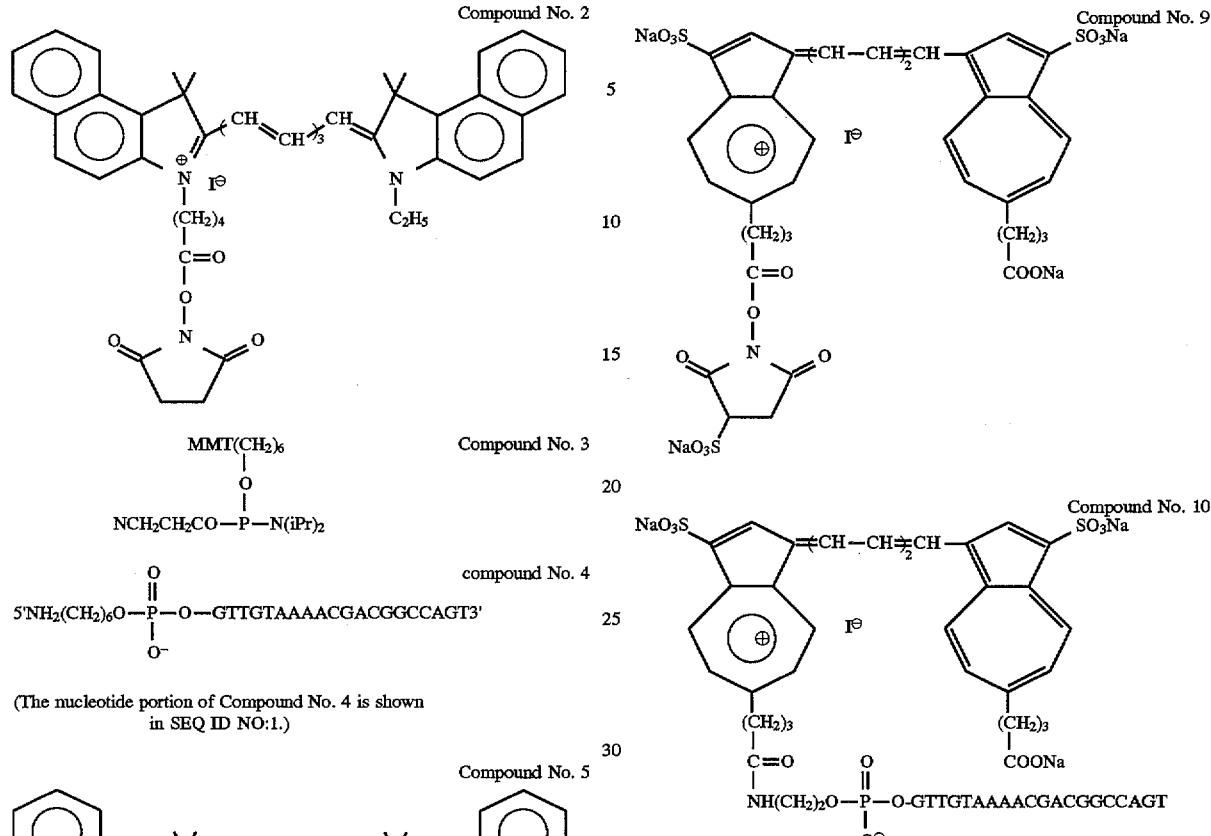

Compound No. 9

Compound No. 10

(The nucleotide portion of Compound No. 10 is shown in SEQ ID NO:1.)

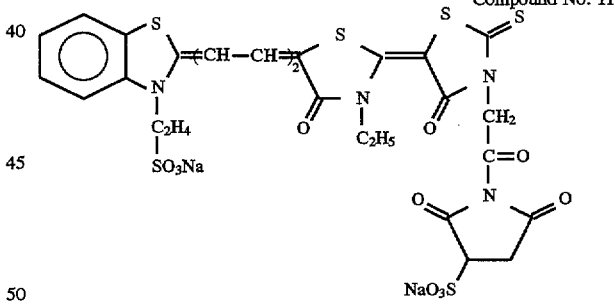

Compound No. 11

-continued

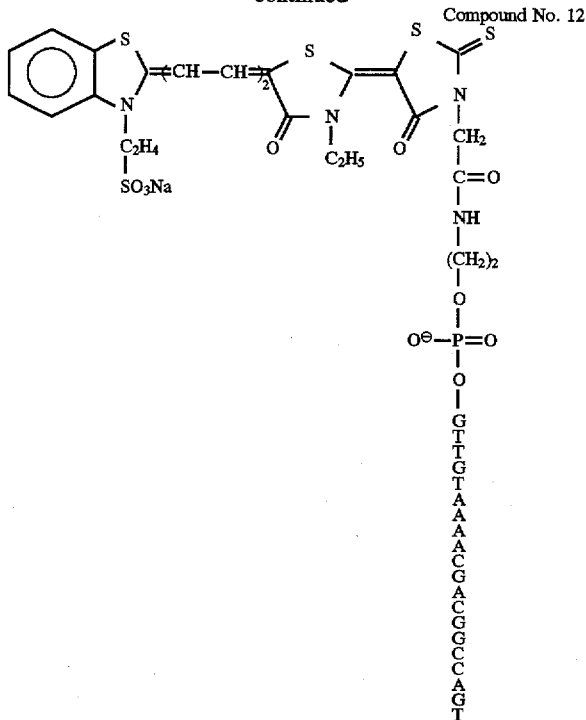

(The nucleotide portion of Compound No. 12 is shown in SEQ ID NO:1.)

EXAMPLE 1

(1) Succinimide esterification of cyanine dye

In 5 ml of dry DMF was dissolved 170 mg of a cyanine dye (Compound No. 1), to which 50 μl of dry pyridine was added. Then, 128 mg of DSC (disuccinimidyl carbonate) was added, followed by stirring at room temperature for 20 hours in the dark. Next, 150 ml of diethyl ether was added to the resulting reaction mixture, and the precipitate was collected, washed with diethyl ether, and then dried. The thus obtained active ester (Compound No. 2) was directly used for a reaction with the nucleic acid.

(2) A 20-meric oligonucleotide was synthesized by a DNA automatic synthesizing machine (381A made by ABI Co., Ltd.), which is complementary to a part of the base sequence of a model target nucleic acid (M13mp18ss DNA). Afterward, a primary amino group was introduced to the 5' terminal of the 20-meric oligonucleotide, using a deoxyuridylic acid derivative monomer (Compound No. 3) instead of using an ordinary amidide reagent to which an amino group was introduced. Cleavage from the CPG support, removal of the protective groups, and purification by high performance liquid chromatography (HPLC), of the oligomer, were carried out in the usual ways.

(3) Bonding of nucleic acid to active ester of cyanine dye

Figure 2:
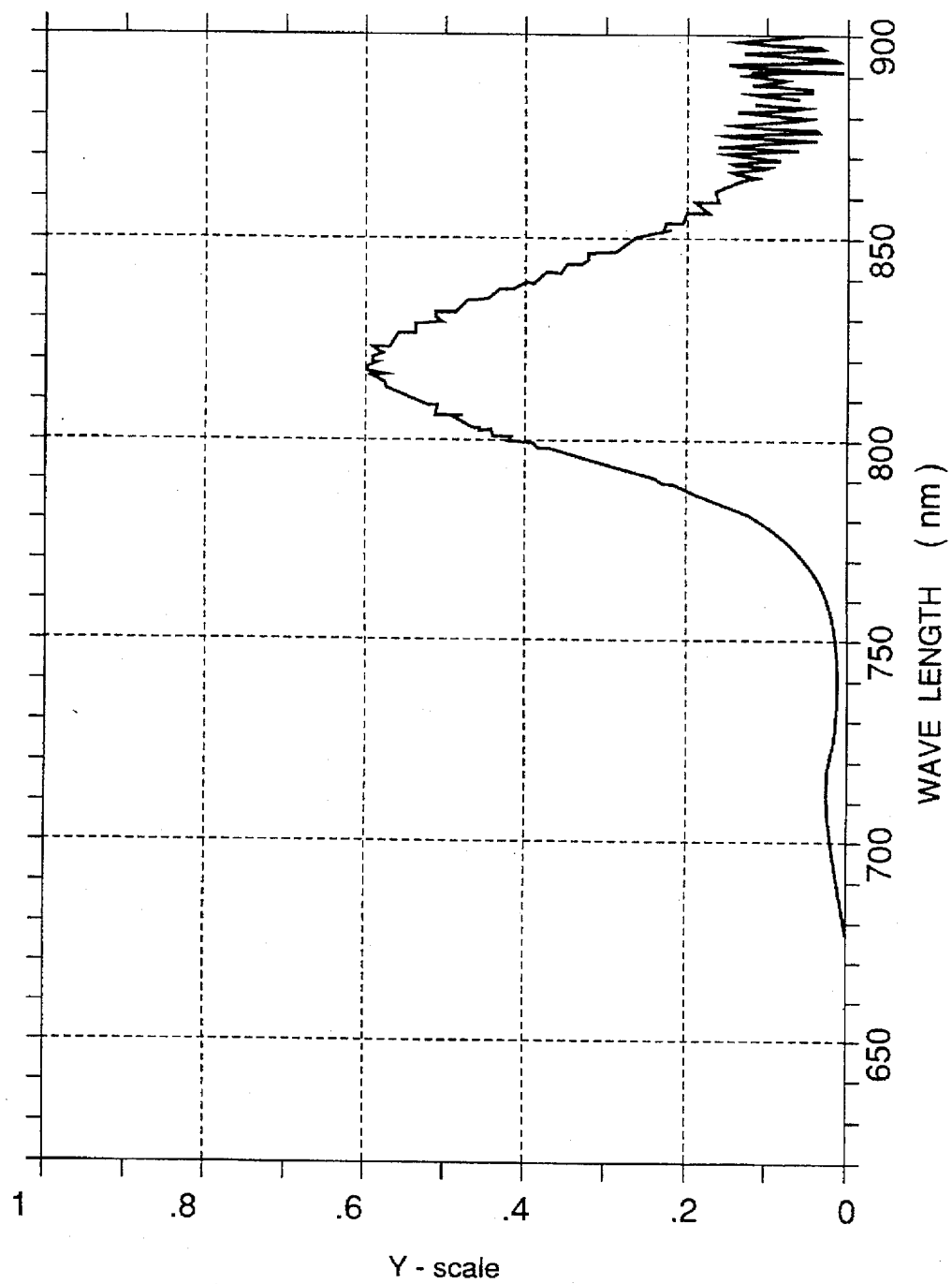
FIG. 2 shows a fluorescence spectrum of Compound No. 5.

200 μg of the above-mentioned oligonucleotide (Compound No. 4) to which a primary amino group was introduced, and 100 μl of a solution of 1M sodium phosphate buffer of pH 7 were mixed with and dissolved in 500 μl of water, and 2 mg of the active ester of the cyanine dye (Compound No. 2) which was previously dissolved in 400 μl of acetonitrile was then slowly added thereto with stirring. After reaction at 40° C. for 24 hours, the product was roughly purified by passing through a gel permeation column NAP-50 made by Pharmacia Co., Ltd., and then purified by HPLC to obtain about 180 μg of a cyanine dye-oligonucleotide composite (Compound No. 5). An absorption spectrum and a fluorescence spectrum of Compound No. 5 are shown in FIGS. 1 and 2, respectively. FIGS. 1 and 2 indicate that Compound No. 5 is most desirable as a fluorescent labeled DNA probe which is excited by a semiconductor laser of 780 nm.

(4) Synthesis of complementary strand

Three oligonucleotide 20-mers, Compounds Nos. 6, 7 and 8 were synthesized by an automatic DNA synthesizer, which were completely complementary to Compound No. 5, mismatched with one base, and mismatched with two bases respectively, and then purified in the usual way. Arrows on the base sequences of the above-mentioned structures of Compound Nos. 7 and 8 denote mismatched positions.

(5) Measurement of melting temperature

In a 50 mM sodium phosphate buffer solution (pH=7.0), a double stranded structure was formed between the oligonucleotide portion of Compound No. 5 and Compound No. 6, and the melting temperature was then measured and determined to be 60° C. For the combination of Compound Nos. 5 and 7 and the combination of Compound Nos. 5 and 8, the melting temperature was measured in the same manner, and determined to be 32.5° C. and 17.5° C., respectively.

(6) Capillary electrophoresis

Figure 3:
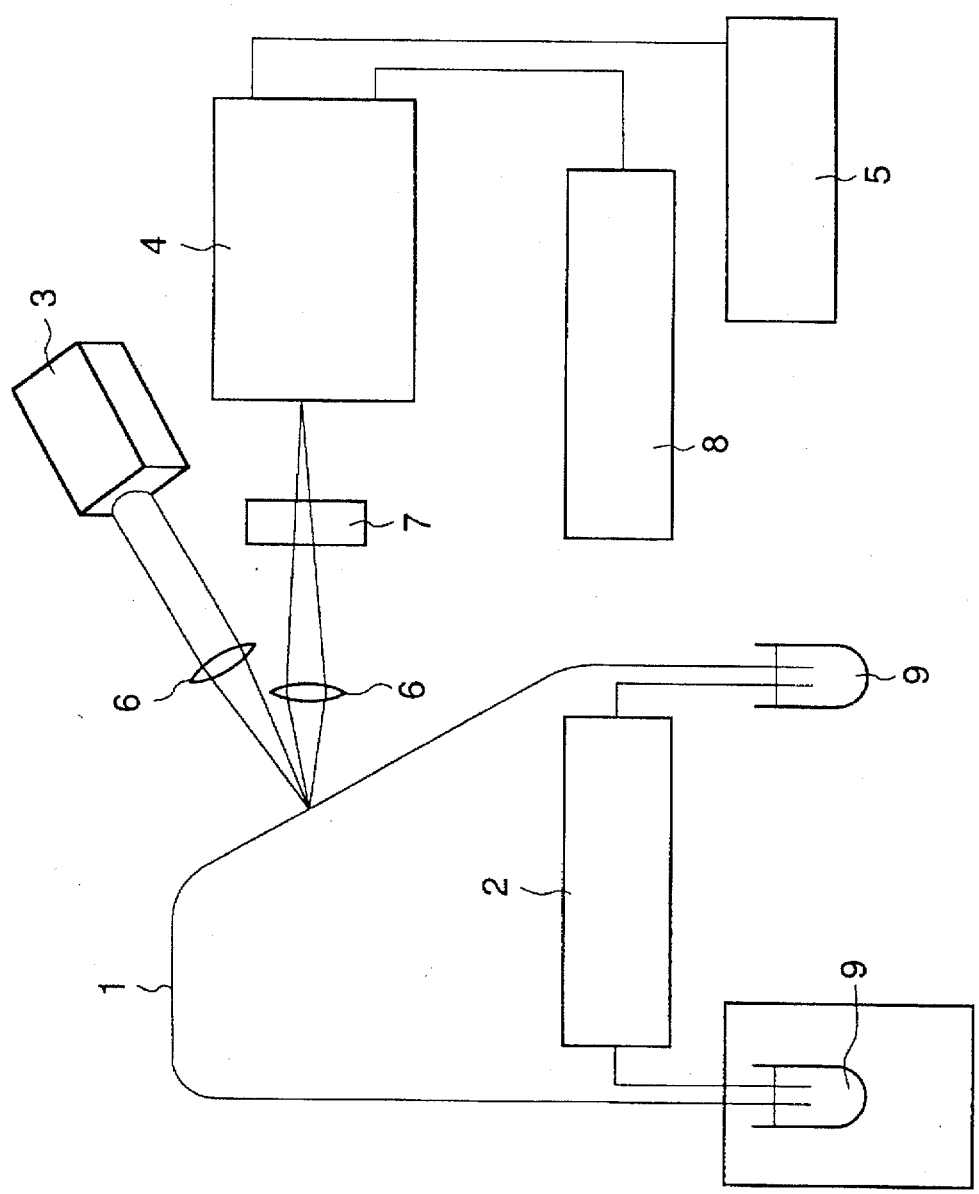
FIG. 3 shows a schematic view of a capillary electrophoresis apparatus.

Capillary electrophoresis was carried out by the use of an apparatus shown in FIG. 3. In this apparatus, a sample was fed to one end of a capillary 1, and a high voltage was applied from a power source 2 to both the ends of the capillary 1 to perform electrophoresis. The nucleic acid moved toward the positive electrode. Next, the fluorescent label of the migrating nucleic acid probe was excited by a laser from a laser source 3, and the generated fluorescence was collected, detected by a photomultiplier 4, and then recorded by a recorder 5. In FIG. 3, Numeral 6 represents a lens, Numeral 7 represents a filter, Numeral 8 represents a power source, and Numeral 9 represents a buffer.

Operating conditions used herein are as follow:

Capillary: Inner diameter=50 μm, outer diameter =375 μm, total length=550 mm, no gel packing Migration distance: 450 mm (detection was done in the capillary)

Electrophoresis voltage: 20 kV

Laser wavelength: 780 nm

Laser output: 10 mW

Electrophoresis solution: 50 mM sodium phosphate buffer solution of pH 7

Amount of injected sample: 1 nl

Filter: 810 nm low-cut filter (a) Single electrophoresis of DNA probe

An 1 nl aliquot of a $5\times10^{-9}$ M solution of Compound No. 5 was injected into the capillary, and the electrophoresis was carried out at a capillary temperature of 30° C., and a single peak was detected at 7.7 minutes of electrophoresis. The detection limit was $8\times10^{-11}$M with S/N=3, and the calculated detection limit amount was $8\times10^{-20}$ mol. That is to say, an extremely trace amount of the DNA probe, as low as 0.1 amol, was detected.

(b) Electrophoresis of DNA probe (Compound No. 5) and complementary strand (Compound No. 6)

Compound No. 5 and Compound No. 6 were mixed to the final concentrations of $1\times10^{-8}$M and $5\times10^{-9}$M respectively, and then the resulting mixed solution was retained at 80° C. for 2 minutes. The temperature of the solution was cooled to room temperature over 1 hour (hybridizing conditions). This solution was subjected to capillary electrophoresis under all the same conditions as in the above-mentioned (a), and as a result, peaks having about the same area intensity were detected at 7.7 minutes and 13.5 minutes. The peak at 7.7 minutes was Compound No. 5 alone, and the peak at 13.5 minutes was a hybrid of Compound Nos. 5 and 6. This result indicates that an extremely trace amount, 0.1 amol, of the target DNA was detected as the hybrid with the probe DNA, B/F-separated from the free probe DNA. In addition, it is also indicated that a cyanine dye labeled fluorescent DNA probe was sufficiently stable under hybridization conditions and capillary electrophoresis conditions.

EXAMPLE 2

Compound No. 5 was mixed with compounds No. 6 and No. 7 to the final concentrations of $1.5 \times 10^{-8}$M, $5 \times 10^{-9}$M and $5 \times 10^{-9}$M respectively. Next, the resulting mixed solution was put in the hybridizing conditions of Example 1 and then heated again at 40° C., and electrophoresis was carried out in a capillary at the controlled temperature of 40° C. (the other conditions were the same as in Example 1). As a result, a peak of the nucleic acid probe was detected at 6.4 minutes, and another peak (a hybrid of Compound Nos. 5 and 6) having a half area intensity of the peak at 6.4 minutes was detected at 12.6 minutes. That is to say, since the electrophoresis was carried out at a temperature (40° C.) which is higher than the melting temperature (32.5° C.) of the hybrid formed between Compound No. 5 and Compound No. 7 having one mismatched base, the hybrid formed between Compound No. 5 and Compound No. 7 was prevented from contaminating the hybrid of Compound Nos. 5 and 6.

EXAMPLE 3

Compound Nos. 5, 6, 7 and 8 were mixed so that the final concentration of Compound No. 5 and the final concentration of Compound Nos. 6, 7 and 8 were $2 \times 10^{-8}$M and $5 \times 10^{-9}$M, respectively. The resulting mixed solution was put under the hybridizing conditions of Example 1, and then cooled to 10° C. Next, 1 nl of the solution was injected into a capillary previously cooled to 10° C.

Simultaneously with the start of capillary electrophoresis, the temperature of the capillary was raised to 40° C. at a ratio of 1° C./minute and then maintained at 40° C. As a result, 4 peaks having similar area intensities were detected at 9.8 minutes (free nucleic acid probe which did not form any hybrid), 11.2 minutes (the nucleic acid probe which once formed a hybrid with Compound No. 8), 24.1 minutes (the nucleic acid probe which once formed a hybrid with Compound No. 7), and 26.6 minutes (the hybrid of Compound Nos. 5 and 6). By gradually raising the temperature of the capillary, detection in compliance with the number of mismatched bases of the nucleic acids was possible.

EXAMPLE 4

Single-stranded DNA of *Escherichia coli* phage M13mp18 of the final concentration of $5 \times 10^{-9}$M and a nucleic acid probe (Compound No. 5) of final concentration of $2 \times 10^{-8}$M were placed under the hybridizing conditions of Example 1, and then cooled to 20° C. Next, capillary electrophoresis was carried out under the following conditions:

Capillary: Inner diameter=50 μm, outer diameter =375 μm, and total length=100 mm Packed gel: 5% polyacrylamide gel (buffer solution for gel preparation: 100 mM of Tris, 250 mM of boric acid and 7M of urea; pH=7.0)

Migration distance: 90 mm (detection was made in the capillary)

Electrophoresis voltage: 2.5 kV

Laser wavelength: 780 nm

Laser output: 10 mW

Amount of injected sample: 1 nl

Filter: 810 nm low-cut filter (a) Single electrophoresis of DNA probe 1 nl of a $5 \times 10^{-8}$M solution of Compound No. 5 was injected into the capillary, and the electrophoresis was carried out with capillary temperature of 30° C. As a result, a single peak was detected at electrophoresis time of 3.2 minutes. With S/N=3, the detection limit was $8 \times 10^{-11}$M as in Example 1, and the detection limit amount was $8 \times 10^{-20}$ mol according to calculation.

(b) Electrophoresis of DNA probe (Compound No. 5) and M13mp18ss DNA 1 nl of a mixture of a DNA probe (Compound No. 5) and M13mp18ss DNA which was prepared and hybridized as mentioned above was injected into a capillary, and capillary electrophoresis was then carried out. As a result, peaks were detected at electrophoresis times of 3.2 minutes and 18.7 minutes, and the ratio of area intensities of these peaks were about 3:1.

These peaks at 3.2 minutes and 18.7 minutes were a peak of the free nucleic acid probe and a peak of the hybrid of the nucleic acid probe and M13mp18ss DNA, respectively. By capillary electrophoresis, DNA derived from a biological source could be B/F-separated by an easy operation and detected with a high sensitivity.

EXAMPLE 5

Figure 4:
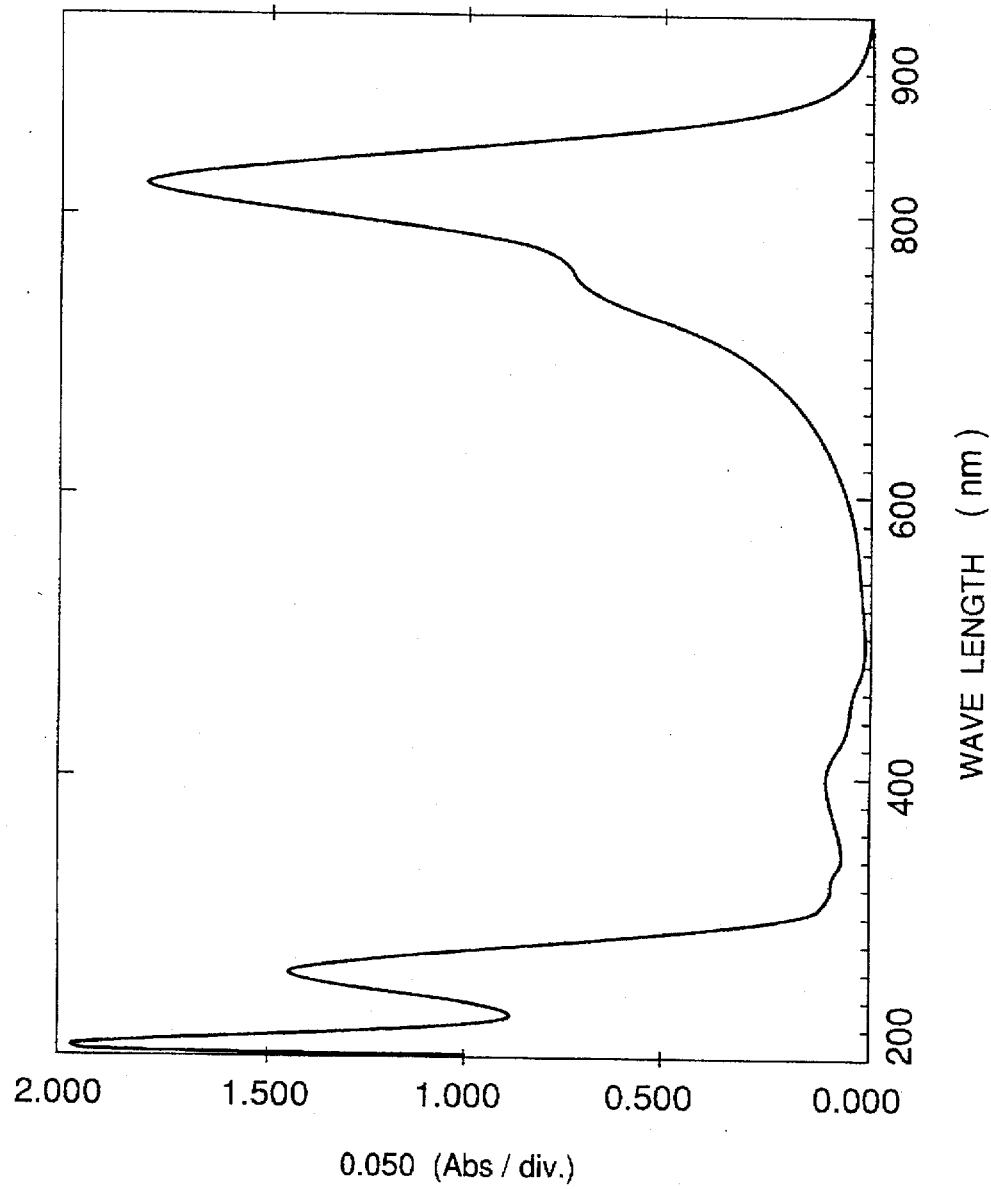
FIG. 4 shows an absorption spectrum of Compound No. 10.
Figure 5:
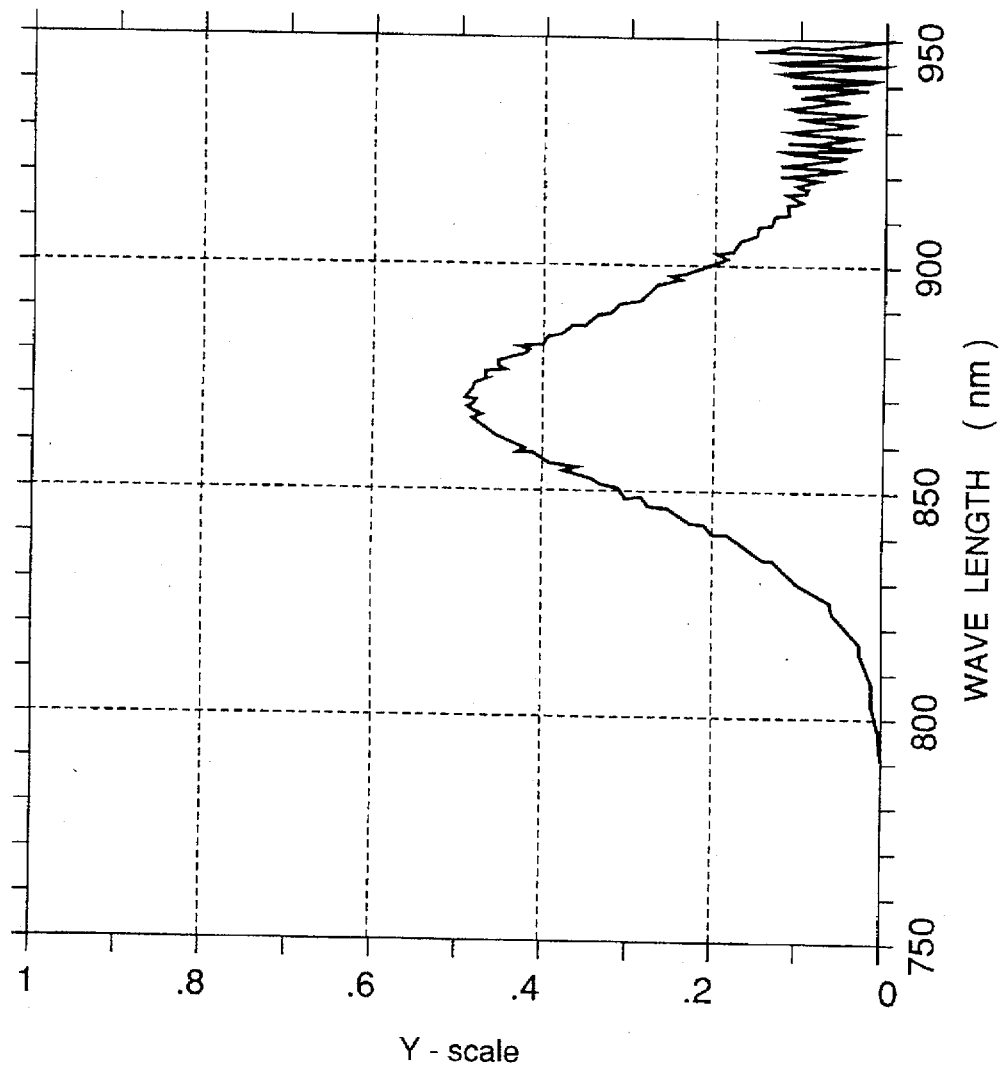
FIG. 5 shows a fluorescence spectrum of Compound No. 10.

A composite (Compound No. 10) of an oligonucleotide (4) having a primary amino group and an active azulene dye ester (Compound No. 9) was obtained in the same manner as in Example 1. An absorption spectrum and a fluorescence spectrum of Compound No. 10 are shown in FIGS. 4 and 5, respectively. FIGS. 4 and 5 indicate that Compound No. 10 is most desirable as a fluorescent labeled DNA probe which can be excited by a semiconductor laser of 830 nm. Melting temperature of the hybrid of Compound No. 10 and Compound No. 6 was 60° C.

Next, Compound No. 10 alone was subjected to capillary electrophoresis under the same conditions as in Example 1 (the excitation light source was a semiconductor laser of 830 nm and 10 mW output). As a result, a single peak was detected at 7.9 minutes. The difference of electrophoresis time of this compound and that of Compound No. 5 in Example 1 is presumably attributed to the difference of characteristics of the dyes.

Afterward, a mixed solution of Compound No. 10 and Compound No. 6 was subjected to electrophoresis under all the same conditions as in Example 1 (an excitation light source was a semiconductor laser of 830 nm, output of 10 mW, and a filter was a 860 nm low-cut filter). As a result, peaks having about the same area intensity were detected at electrophoresis times of 7.9 minutes and 13.8 minutes. Thus, when the DNA probe labeled with an azulene fluorescent dye was employed, the target nucleic acid could be B/F-separated by capillary electrophoresis without complicated operations and detected with high sensitivity using a semiconductor laser of 830 nm as the light source. It was also apparent that the DNA probe labeled with an azulene fluorescent dye was stable under the hybridization conditions and capillary electrophoresis conditions.

EXAMPLE 6

A composite (Compound No. 12) of an oligonucleotide (Compound No. 4) having a primary amino group and an active ester of a trinuclear type dye (Compound No. 11) was obtained in accordance with the same procedure as in Example 1. The absorption maximum and the fluorescence maximum wavelength of Compound No. 12 were 636 nm and 725 nm, respectively. Furthermore, the melting temperature of the hybrid of Compound No. 12 and Compound No. 6 was 58° C. Next, Compound No. 12 alone was subjected to capillary electrophoresis under the same conditions as in Example 1 (an excitation light source was an He-Ne laser of 630 nm having an output of 10 mW, and a filter was a 680 nm low-cut filter). As a result, a single peak was detected at 7.5 minutes.

The difference of the electrophoresis time of this compound and that of Compound No. 5 in Example 1 is presumably due to the difference of characteristics of the dyes. Next, a mixed solution of Compound No. 12 and Compound No. 6 was subjected to electrophoresis under all the same conditions as in Example 1 (an excitation light source was an He-Ne laser of 630 nm having an output of 10 mW). As a result, peaks having about the same area intensity were detected at electrophoresis times of 7.5 minutes and 13.5 minutes. Thus, when the DNA probe labeled with a trinuclear type fluorescent dye was employed, the target nucleic acid could be B/F-separated without complicated operations by capillary electrophoresis, and then detected with a high sensitivity using the He-Ne laser of 630 nm as the light source. It was also apparent that the DNA probe labeled with a trinuclear type fluorescent dye was stable under the hybridizing conditions and capillary electrophoresis conditions.

EXAMPLE 7

Compound Nos. 5, No. 6 and No. 10 were mixed at the final concentration of $5\times10^{-9}$M, $1\times10^{-8}$M, and $5\times10^{-9}$M, respectively, and 1 nl of the resulting mixture was subjected to electrophoresis under the same conditions as in Example 5 except that the excitation light source was semiconductor lasers of 780 nm and 830 nm positioned each other at an angle of 90°, and the detecting devices were correspondingly arranged. As a result, peaks having about the same area intensity were detected at 12.5 minutes and 13.8 minutes. Thus, when a cyanine fluorescent dye labeled DNA probe and an azulene fluorescent dye labeled DNA probe were used, simultaneous two wavelength detection was possible in capillary electrophoresis using the semiconductor laser of 780 nm and 830 nm.

EXAMPLE 8

Three kinds of nucleic acid probes (Compound Nos. 5, 10 and 12) were each dissolved in a 100 mM sodium phosphate buffer solution (pH 7.0) to the concentration of $5\times10^{-9}$M, and the respective solutions were stored at 4° C. and at room temperature. They were analyzed by capillary electrophoresis every two months for six months, and electrophoresis times and area intensity did not change from their initial values. Thus, the DNA probe labeled with a cyanine fluorescent dye, the DNA probe labeled with a trinuclear type fluorescent dye and the DNA probe labeled with an azulene fluorescent dye exhibited excellent storage stability.

According to the present invention, a target nucleic acid can be detected by much easier operations in a shorter time with a higher sensitivity as compared with conventional techniques. Furthermore, one point mismatch of the bases can also be detected by controlling the temperature of a capillary electrophoresis apparatus or by gradually raising the temperature. In addition, when a cyanine dye, a trinuclear type dye or an azulene dye is used as a fluorescent label for a nucleic acid probe, a nucleic acid probe having excellent storage stability can be prepared, and the stable detection can be achieved without any adsorption of the probe on the capillary.

---

What is claimed is:

1. A process for detecting a target nucleic acid comprising the steps of:
   (a) hybridizing a labeled single-stranded nucleic acid probe with a target single-stranded nucleic acid in a sample solution to form a reaction mixture in which at least one of a matched hybrid and a mismatched hybrid may be present;
   (b) subjecting the reaction mixture to capillary electrophoresis conducted at a temperature at which the mismatched hybrid melts and releases labeled probe but the matched hybrid does not melt to separate the matched hybrid from the labeled probe released from the mismatched hybrid; and
   (c) detecting the matched hybrid by the label moiety of the nucleic acid probe bound thereto.

2. The process for detecting a nucleic acid according to claim 1, wherein in the step (b), the temperature is gradually raised from a temperature at which a mismatched hybrid having the lowest melting temperature will melt, to a temperature at which a mismatched hybrid having the highest melting temperature will melt.

3. The process according to claim 1, wherein the temperature is 5° to 25° C. lower than a temperature at which the matched hybrid melts.

4. A process for detecting a target single-stranded nucleic acid comprising the steps of:
   providing a sample liquid which contains a target single-stranded nucleic acid;
   adding to the sample liquid a nucleic acid probe having a label moiety which comprises a fluorescent dye to form a hybrid between the target single-stranded nucleic acid and the probe;
   subjecting the liquid to capillary electrophoresis to separate the hybrid from the free probe which is unhybridized to the target single-stranded nucleic acid; and
   detecting the hybrid separated from the unhybridized probe by using fluorescent light emitted from the fluorescent dye in the label moiety of the hybrid, wherein the fluorescent dye is a compound selected from compounds represented by the general formulas (I), (II), (III) and (IV):

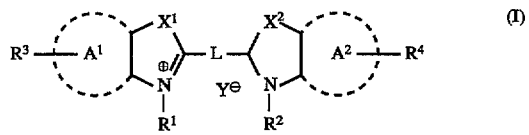

wherein $X^1$ and $X^2$ are each independently an oxygen atom, a sulfur atom, a selenium atom, C=O, CH=CH, $NR^5$ or $CR^6R^7$, wherein $R^5$ to $R^7$ are each independently an alkyl group, an aryl group or an aralkyl group; $A^1$ and $A^2$ are each independently an aromatic ring comprising carbon atoms and hydrogen atoms, or another aromatic ring comprising carbon atoms, hydrogen atoms, a nitrogen atom and/or an oxygen atom and/or a sulfur atom; $R^1$, $R^2$, $R^3$ and $R^4$ are each independently a hydrogen atom, a halogen atom, a substituted or unsubstituted alkyl group, an alkoxy group, a substituted or unsubstituted aryl group, or a substituted or unsubstituted amino group; L is a methine chain comprising 1 to 8 substituted or unsubstituted methine radicals; and $Y^-$ is an acid radical;

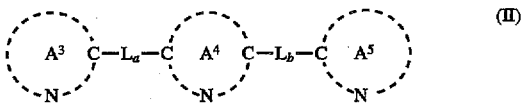

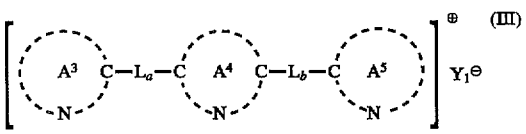

wherein $A_3$, $A_4$ and $A^5$ are each a substituted or unsubstituted five-membered or six-membered aromatic heterocycle having at least one or two nitrogen atoms, or a condensed ring thereof; $L_a$ and $L_b$ are each a methane chain comprising 1 to 6 substituted or unsubstituted methine radicals, and one of $L_a$ and $L_b$ may be omitted, so that two aromatic heterocycles are directly bonded to each other; and $Y^-$ is an acid radical; and

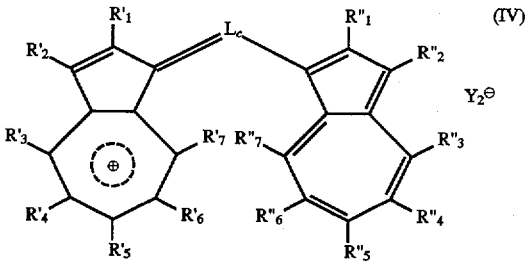

wherein $R'_1$ to $R'_7$ and $R''_1$ to $R''_7$ are each independently a hydrogen atom, a halogen atom, a substituted or unsubstituted alkyl group, an alkoxy group, a substituted or unsubstituted aryl group, an alkenyl group, a substituted or unsubstituted aralkyl group, a substituted or unsubstituted styryl group, an arylazo group, a sulfonate group, an amino group, a nitro group, hydroxy, carboxyl or cyano, and $R'_1$ to $R'_7$ or $R''_1$ to $R''_7$ may be bonded to each other to form a substituted or unsubstituted condensed ring; $Y_2^-$ is an anion; and $L_c$ is a methine chain comprising 1 to 8 substituted or unsubstituted methine radicals.

5. The process according to claim 4, further comprising the step of heating the liquid at a temperature for denaturing a mismatch-hybrid between the probe and a single-stranded nucleic acid whose sequence is different from that of the target single-stranded nucleic acid.

6. The process according to claim 5, wherein the heating step is carried out in the step for electrophoresis.

7. The process according to claim 5, wherein the heating step is carried out prior to the step of electrophoresis.

8. A process for detecting a matched hybrid formed by a target single-stranded nucleic acid and a labeled single-stranded nucleic acid probe from a mismatched hybrid formed by the labeled probe and a nucleic acid whose base sequence is different from that of the target nucleic acid comprising the steps of:

(a) hybridizing the labeled nucleic acid probe with a single-stranded nucleic acid to form a reaction mixture in which at least one of a matched hybrid and a mismatched hybrid may be present;

(b) melting only the mismatched hybrid to release the labeled probe;

(c) subjecting the reaction mixture to capillary electrophoresis to separate the matched hybrid and the labeled probe released from the molten mismatched hybrid utilizing the difference of migration speed of the matched hybrid and the labeled probe in the capillary; and (d) detecting the matched hybrid through the label moiety of the probe bound to the matched hybrid in the capillary.

9. The process according to claim 8, wherein the capillary electrophoresis is conducted at a temperature at which the mismatched hybrid melts but the matched hybrid does not melt.

10. The process according to claim 9, wherein the temperature is 5° to 25° C. lower than a temperature at which the matched hybrid melts.

* * * * *

UNITED STATES PATENT AND TRADEMARK OFFICE
CERTIFICATE OF CORRECTION

PATENT NO. : 5,679,516

DATED : October 21, 1997

INVENTOR(S) : TADASHI OKAMOTO ET AL.

It is certified that error appears in the above-identified patent and that said Letters Patent is hereby corrected as shown below:

COLUMN 1

Line 37, "bacterium in an infection" should read --bacteria in an infectious--.
Line 42, "problems" should read --problems in--.
Line 43, "much" should read --very--.
Line 45, "that" should be deleted.

COLUMN 2

Line 24, "tens" should read --tenths of a--.
Line 30, "includes" should read --include--.
Line 41, "providing" should read -- by providing a --.
Line 46, "samples" should read --sample--.
Line 55, "subjecting" should read --subjecting the--.

COLUMN 3

Line 7, "PREFFERRED" should read --PREFERRED--.
Line 34, "aimed" should read --desired--.
Line 58, "iS" should read --is--.

COLUMN 4

Line 8, "reaction" should read --reaction of--.
Line 16, "mismatch" should read --mismatched--.
Line 19, "aimed" should read --desired--.
Line 33, "mismatch" should read --mismatched--.

UNITED STATES PATENT AND TRADEMARK OFFICE
CERTIFICATE OF CORRECTION

PATENT NO. : 5,679,516

DATED : October 21, 1997

INVENTOR(S) : TADASHI OKAMOTO ET AL.

It is certified that error appears in the above-identified patent and that said Letters Patent is hereby corrected as shown below:

COLUMN 5

Line 4, "quite" should read --very--.
    Line 19, "been" (first occurrence) should be deleted.

COLUMN 6

Line 35, "the water-solubility of" should be deleted.

COLUMN 8

Line 13, "fluorosulfonate-ion" should read
      --fluorosulfonate ion--.

COLUMN 9

Line 22, "$I^{\ominus}$" should read --$I^{\ominus}$--.

COLUMN 11

Line 17, "dye" should read --dyes--.
    Lines 18-19, "heterocycles" should read --heterocycles
      are--.

COLUMN 21

Line 17, "$\eta$-naphthylazo" should read $\beta$-naphthylazo--.
    Line 39, "the water-solubility of" should be deleted.

UNITED STATES PATENT AND TRADEMARK OFFICE
CERTIFICATE OF CORRECTION

PATENT NO.   : 5,679,516

DATED        : October 21, 1997

INVENTOR(S): TADASHI OKAMOTO ET AL.

It is certified that error appears in the above-identified patent and that said Letters Patent is hereby corrected as shown below:

COLUMN 27

Line 48, "→" should be deleted.

COLUMN 31

Line 43, "ratio" should read --rate--.

COLUMN 33

Line 32, "No. 6 and No. 10." should read --6 and 10--.

COLUMN 34

Line 2, "positioned" should read --positioned with respect to--.

COLUMN 35

Line 40, "releases" should read --releases the--.

UNITED STATES PATENT AND TRADEMARK OFFICE
CERTIFICATE OF CORRECTION

PATENT NO. : 5,679,516

DATED : October 21, 1997

INVENTOR(S): TADASHI OKAMOTO ET AL.

It is certified that error appears in the above-identified patent and that said Letters Patent is hereby corrected as shown below:

<u>COLUMN 36</u>

Line 65, "$A_3, A_4$" should read --$A^3, A^4$--.

Signed and Sealed this

Twenty-third Day of June, 1998

Attest:

BRUCE LEHMAN

Attesting Officer

Commissioner of Patents and Trademarks